United States Patent
Mougin et al.

(10) Patent No.: US 8,178,079 B2
(45) Date of Patent: May 15, 2012

(54) ETHYLENE COPOLYMERS, COMPOSITIONS CONTAINING SAID COPOLYMERS AND TREATMENT METHOD

(75) Inventors: Nathalie Mougin, Paris (FR); Gwenaëlle Jegou, Livry Gargan (FR)

(73) Assignee: L'Oreal S.A., Paris (FR)

( * ) Notice: Subject to any disclaimer, the term of this patent is extended or adjusted under 35 U.S.C. 154(b) by 1410 days.

(21) Appl. No.: 11/631,119

(22) PCT Filed: Jul. 1, 2005

(86) PCT No.: PCT/FR2005/001699
§ 371 (c)(1),
(2), (4) Date: Mar. 6, 2007

(87) PCT Pub. No.: WO2006/013268
PCT Pub. Date: Feb. 9, 2006

(65) Prior Publication Data
US 2008/0014154 A1  Jan. 17, 2008

Related U.S. Application Data

(60) Provisional application No. 60/587,553, filed on Jul. 14, 2004.

(30) Foreign Application Priority Data

Jul. 2, 2004  (FR) ..................... 04 51411

(51) Int. Cl.
*A61K 8/72* (2006.01)
*A61K 31/74* (2006.01)
(52) U.S. Cl. .............. 424/59; 424/70.11; 424/78.03; 424/78.31; 424/78.35; 526/242; 526/248; 526/256; 526/266; 526/274; 526/286; 526/319
(58) Field of Classification Search ............ 424/59, 424/70.11, 78.03, 78.31, 78.35; 526/242, 526/248, 256, 266, 274, 286, 319
See application file for complete search history.

(56) References Cited

U.S. PATENT DOCUMENTS

| | | | |
|---|---|---|---|
| 4,237,253 A | 12/1980 | Jacquet et al. | |
| 4,324,780 A | 4/1982 | Jacquet et al. | |
| 5,603,926 A * | 2/1997 | Matsumoto et al. | 424/70.15 |
| 5,608,021 A | 3/1997 | Uchiyama et al. | |
| 7,160,947 B2 | 1/2007 | Claesson et al. | |
| 2004/0052746 A1 | 3/2004 | Tamareselvy et al. | |

FOREIGN PATENT DOCUMENTS

| | | |
|---|---|---|
| EP | 0 372 546 B1 | 6/1990 |
| EP | 0 947 244 B1 | 10/1999 |
| FR | 2 419 947 | 10/1979 |
| JP | 6-219921 | 8/1994 |
| JP | 7-285831 | 10/1995 |
| JP | 2000-302649 | 10/2000 |
| JP | 2001-181354 A | 7/2001 |
| JP | 2002-256030 A | 9/2002 |
| JP | 2002-284627 | 10/2002 |
| JP | 2002-322219 | 11/2002 |
| JP | 2003-55164 | 2/2003 |
| WO | WO 03/075867 A1 | 9/2003 |

OTHER PUBLICATIONS

Japanese Office Action for Application No. JP 2007-518650 dated Nov. 16, 2010.
International Search Report for PCT/FR2005/001699), dated Jan. 24, 2006.
Patent Abstracts of Japan, vol. 1999, No. 12, Oct. 29, 1999 (JP 11 181029 A).
English language abstract of JP 7-285831, Oct. 31, 1995.
English language abstract of JP 2000-302649, Oct. 31, 2000.
English language abstract of JP 2002-284627, Oct. 3, 2002.
English language abstract of JP 2002-322219, Nov. 8, 2002.
English language abstract of JP 2003-55164, Feb. 26, 2003.

* cited by examiner

*Primary Examiner* — Robert D. Harlan
(74) *Attorney, Agent, or Firm* — Finnegan, Henderson, Farabow, Garrett & Dunner, LLP

(57) ABSTRACT

The invention relates to novel ethylene copolymers comprising 10-60% polyethylenglycol (meth)acrylate monomers and 40-90% substantially cationic monomer. Compositions, in particular cosmetic or pharmaceutical compositions, containing the inventive copolymers and a cosmetic treatment method using said copolymers are also disclosed.

40 Claims, No Drawings

ETHYLENE COPOLYMERS, COMPOSITIONS CONTAINING SAID COPOLYMERS AND TREATMENT METHOD

CROSS REFERENCE TO RELATED APPLICATIONS

This application is a National Phase application based on PCT/FR2005/001699 filed on Jul. 1, 2005, the contents of which are incorporated herein by reference, and claims the priority of French Application No. 0451411, filed Jul. 2, 2004, and the benefit of U.S. Provisional Application No. 60/587,553, filed Jul. 14, 2004, the contents of both of which are incorporated herein by reference.

The present invention relates to novel polymers, to their use especially in cosmetics, and to compositions comprising them.

It is known practice to use polymers in cosmetics, and especially in haircare, for example to give the hair hold or body. In the field of "rinse-out" hair compositions, such as shampoos or hair conditioners, water-soluble synthetic cationic polymers are especially used, which are known to give the hair good cosmetic properties; however, these polymers do not provide any hair shaping effect. This is likewise the case for cationic polymers of natural origin such as modified guars, which also provide a cosmetic nature without allowing hair shaping. Compositions that afford styling and that have an acceptable cosmetic nature are not known in the field of rinse-out compositions. In the field of "leave-in" hair compositions, such as styling products of the styling lacquer, gel or spray type, there is an ongoing search for polymers that give the hair styling effects and hold. Polymers containing amine units, such as polymers based on vinylpyrrolidone and dimethylaminoethyl methacrylate (Gaffix polymers) are known in styling products. However, the compositions obtained have insufficient hold over time. Polymers of Luviquat type, based on quaternized vinylimidazole and vinylpyrrolidone, are also known, and provide softness, but thicken the compositions.

The aim of the present invention is to propose polymers capable of providing a real styling effect while at the same time conserving an acceptable cosmetic nature for compositions, and especially sparingly viscous polymers that only slightly modify the viscosity of the compositions comprising them.

After considerable research, the Applicant has demonstrated that the use of polymers comprising, inter alia, monomers of the polyethylene glycol (meth)acrylate type as defined below, can allow the preparation of styling compositions with an adequate cosmetic nature. Polymers containing polyethylene glycol (meth)acrylate (MPEG) units are described in the prior art. Thus, EP 372 546 discloses copolymers based on MPEG and monomers of C1-C8 alkyl(meth) acrylamide type, which may comprise cationic monomers. However, these polymers comprise only a small proportion of cationic monomers, which does not allow them to generate adequate cosmetic effects, especially deposition on the hair that is sufficient to provide the desired properties.

It is to the Applicant's credit to have noticed that it is preferable to use polymers comprising high cationic charge contents in order to obtain a satisfactory deposit of said polymer on the hair.

Document JP2002-322 219 describes polymers containing MPEG units in combination with hydrophobic monomers based on polypropylene glycol (PPO) or polytetramethylene oxide, and cationic monomers. However, it has been found that these polymers comprising hydrophobic monomers do not allow satisfactory cosmetic properties to be obtained.

A composition comprising cationic polymers in which the monomers of PEG type are combined with monomers comprising quaternary amine units is also known from patent JP2002-284 627. However, the presence of quaternary units may induce, gradually in the course of applications, extra deposition that may, in certain cases, harm the cosmetic quality of the composition. Moreover, these polymers contain a low content of cationic charge, of about 0.5% to 6%, which does not allow optimum affinity for the hair.

JP2003-055 164 also discloses polymers containing units of MPEG type; however, these polymers are crosslinked, which makes controlling their synthesis difficult.

Document JP2000-302 649 describes a haircare composition comprising a polymer that comprises cationic or amphoteric monomers, monomers with a polyether group, especially of PEG or PPO type, and also optional monomers that may be mainly hydrophobic (for example stearyl methacrylate).

Haircare compositions comprising a polymer that comprises monomers of MPEG type in combination with ionic, cationic or amphoteric monomers, and additional monomers of C1-C24 alkyl(meth)acrylate type, which are mainly hydrophobic, are also known from patent JP07-285 831.

However, the presence of hydrophobic comonomers, for example of butyl or stearyl acrylate type, does not make it possible to obtain adequate cosmetic properties, and especially does not make it possible to obtain good disentangling of wet hair, just after shampooing.

Patent application WO 03/075 867 is also known, which describes linear block copolymers comprising a poly(alkylene glycol) block surrounded by two ethylenic blocks. These polymers have the drawback of having a central block of poly(alkylene glycol) type of high mass, which gives the polymer high crystallinity, which may lead to opaque products and/or products of greasy nature.

The Applicant has discovered novel polymers that can give a styling and conditioning effect to cosmetic haircare products.

Surprisingly, the polymers according to the invention have advantageous cosmetic properties, for example during application in a formulation of shampoo type; specifically, it has been found that the hair disentangles easily during shampooing, and that the hair is soft; after drying, the compositions according to the invention also allow, once the hair has dried, particularly advantageous shaping of the hair.

Without wishing to be bound by the present explanation, it may be considered that this may be due especially to the presence of PEG (meth)acrylate (MPEG) units in the polymer chain, these units largely contributing to the obtained effect. Specifically, it has been found that this effect is not obtained with a simple mixture of cationic polymer and of polymer of PEG type.

One subject of the present invention is thus an ethylenic copolymer consisting essentially, as a weight percentage relative to the total weight of the polymer:

a) from 10% inclusive to 60% exclusive by weight of at least one monomer of formula (I) as defined below, and/or salts thereof;

b) from 40% exclusive to 90% inclusive by weight of at least one "essentially cationic" monomer and/or salts thereof, chosen from:
  (i) one or more cationic monomers of formula (IIa),
  (ii) one or more amphoteric monomers of formulae (IIc) and (IId), and
  (iii) a mixture of one or more cationic monomers of formula (IIa) with one or more anionic monomers chosen from maleic anhydride and/or those of formula (IIb);

and/or with one or more amphoteric monomers chosen from those of formulae (IIc) and (IId);
and also the salts of said copolymer.

Another subject of the invention is a composition comprising, in a physiologically acceptable medium, at least one such copolymer.

The present invention has the advantage of proposing polymers that are generally conveyable in water, i.e. water-soluble or water-dispersible, which allows them to be used advantageously in cosmetic compositions, especially for skincare or haircare, which are generally water-based.

The term "water-soluble" means that the polymer forms a clear solution in water, in a proportion of at least 5% by weight, at 25° C.

The term "water-dispersible" means that the polymer forms in water, at a concentration of 5% by weight, at 25° C., a stable suspension or dispersion of fine, generally spherical particles. The mean size of the particles constituting said dispersion is less than 1 μm and more generally ranges between 5 and 400 nm and preferably from 10 to 250 nm. These particles sizes are measured by light scattering.

In the rest of the present description, the term "cyclic radical" means a monocyclic or polycyclic radical, which may be in the form of one or more saturated and/or unsaturated, optionally substituted rings (for example cyclohexyl, cyclodecyl, benzyl or fluorenyl), but also a radical that comprises one or more of said rings (for example p-tert-butylcyclohexyl or 4-hydroxybenzyl).

The term "saturated and/or unsaturated radical" means totally saturated radicals, totally unsaturated radicals, including aromatic radicals, and also radicals comprising one or more double and/or triple bonds, the rest of the bonds being single bonds.

The ethylenic copolymer according to the invention thus comprises at least one monomer of formula (I), which may be present alone or as a mixture:

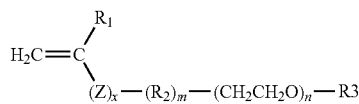
(I)

in which:
R1 is a hydrogen atom or a linear or branched hydrocarbon-based radical, of the type $C_pH_{2p+1}$, with p being an integer between 1 and 12 inclusive;
Z is a divalent group chosen from —COO—, —CONH—, —CONCH$_3$—, —OCO—, —O—, —SO$_2$—, —CO—O—CO— and —CO—CH$_2$—CO—;
x is 0 or 1;
R2 is a saturated or unsaturated, optionally aromatic, linear, branched or cyclic carbon-based divalent radical of 1 to 30 carbon atoms, possibly comprising 1 to 18 heteroatoms chosen from O, N, S, F, Si and P;
m is 0 or 1;
n is an integer between 3 and 300 inclusive;
R3 is a hydrogen atom or a saturated or unsaturated, optionally aromatic, linear, branched or cyclic carbon-based radical of 1 to 30 carbon atoms, possibly comprising 1 to 20 heteroatoms chosen from O, N, S, F, Si and P;
and salts thereof.

R1 may especially represent a methyl, ethyl, propyl or butyl radical. Preferably R1 represents hydrogen or a methyl radical.

Preferably, Z represents COO or CONH.
Preferably, x is equal to 1.

In the radical R2, the heteroatom(s), when they are present, may be intercalated in the chain of said radical R2, or alternatively said radical R2 may be substituted with one or more groups comprising them such as hydroxy or amino (NH2, NHR' or NR'R" with R' and R", which may be identical or different, representing a linear or branched C1-C22 alkyl, especially methyl or ethyl).

R2 may especially be:
an alkylene radical such as methylene, ethylene, propylene, n-butylene, isobutylene, tert-butylene, n-hexylene, n-octylene, n-dodecylene, n-octadecylene, n-tetradecylene or n-docosanylene;

a phenylene radical —C$_6$H$_4$— (ortho, meta or para), optionally substituted with a C1-C12 alkyl radical optionally comprising 1 to 25 heteroatoms chosen from O, N, S, F, Si and P; or alternatively a benzylene radical —C$_6$H$_4$—CH$_2$—, optionally substituted with a C1-C12 alkyl radical optionally comprising 1 to 8 heteroatoms chosen from O, N, S, F, Si and P;

a pyridinium radical of formula:

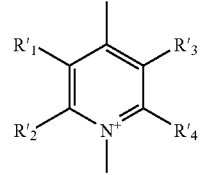

with R'1 to R'4, which may be identical or different, chosen from H and a C1-C12 alkyl radical optionally comprising 1 to 8 heteroatoms chosen from O, N, S, F, Si and P; R'1 to R'4 may especially be methyl and/or ethyl;

a radical of formula —CH$_2$—O—CO—O—, CH$_2$—CH$_2$—O—CO—O—, —CH$_2$—CO—O—, —CH$_2$—CH$_2$—CO—O—, —CH$_2$—O—CO—NH—, —CH$_2$—CH$_2$—O—CO—NH—; —CH$_2$—NH—CO—NH—, —CH$_2$—CH$_2$—NH—CO—NH—; —CH$_2$—CHOH—, —CH$_2$—CH$_2$—CHOH—, —CH$_2$—CH$_2$—CH(NH$_2$)—, —CH$_2$—CH(NH$_2$)—, —CH$_2$—CH$_2$—CH(NHR')—, —CH$_2$—CH(NHR')—, —CH$_2$—CH$_2$—CH(NR'R")—, —CH$_2$—CH(NR'R")—, —CH$_2$—CH$_2$—CH$_2$—NR'—, —CH$_2$—CH$_2$—CH$_2$—O—; —CH$_2$—CH$_2$—CHR'—O— with R' and R" representing a linear or branched C1-C22 alkyl optionally comprising 1 to 12 heteroatoms chosen from O, N, S, F, Si and P;

or a mixture of these radicals.

Preferably, n is between 5 and 200 inclusive and better still between 7 and 100 inclusive, or even between 9 and 50 inclusive.

Preferably, R3 is a hydrogen atom; a benzyl or phenyl radical optionally substituted with a C1-C12 alkyl radical optionally comprising 1 to 8 heteroatoms chosen from O, N, S, F, Si and P; a C1-C30 and especially C1-C22 or even C2-C16 alkyl radical, optionally comprising 1 to 18 heteroatoms chosen from O, N, S, F, Si and P.

These benzyl, phenyl or alkyl radicals may especially comprise a function chosen from the following functions:

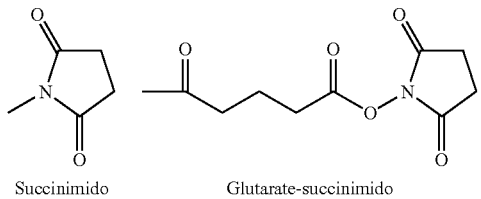

Succinimido     Glutarate-succinimido

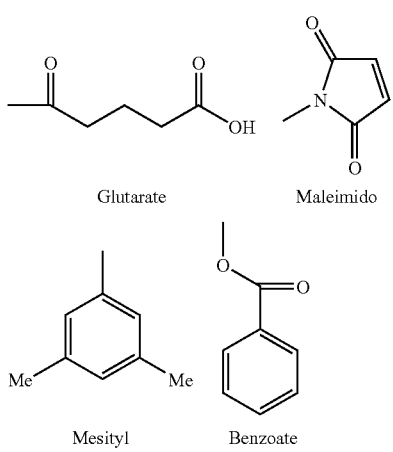

Glutarate     Maleimido

Mesityl     Benzoate

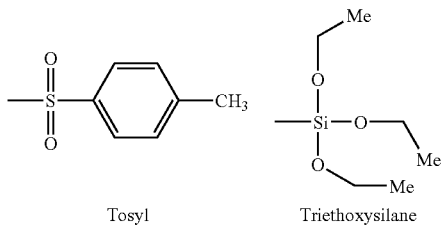

Tosyl     Triethoxysilane

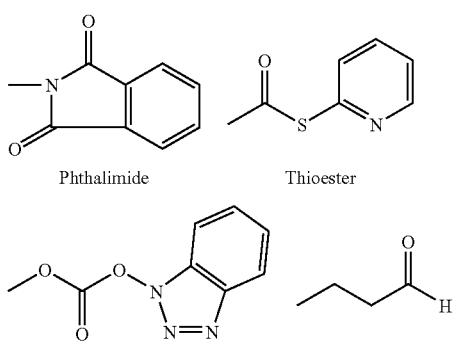

Phthalimide     Thioester

Benzotriazole carbonate     Butyraldehyde

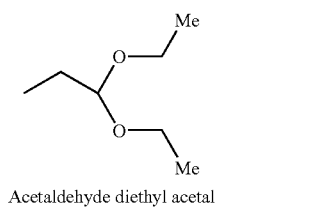

Acetaldehyde diethyl acetal

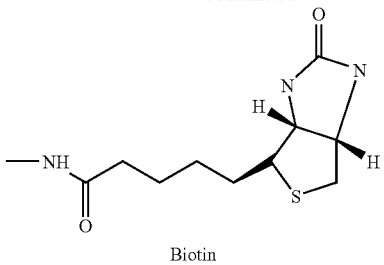

Biotin

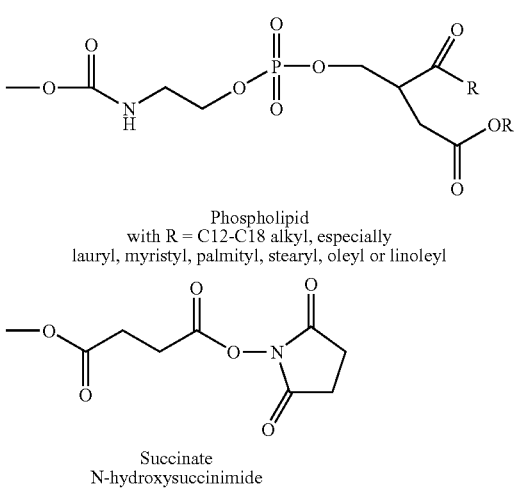

Phospholipid
with R = C12-C18 alkyl, especially
lauryl, myristyl, palmityl, stearyl, oleyl or linoleyl Succinate
N-hydroxysuccinimide or alternatively chosen from —SO$_3$H, —COOH, —PO$_4$, —NR5R6 and —N$^+$R5R6R7, with R5, R6 and R7, independently of each other, chosen from H and linear, branched or cyclic C1-C18 alkyls, especially methyl optionally comprising one or more heteroatoms or alternatively bearing protective groups such as t-butyloxycarbonyl (also known as BOC) or 9-fluorenylmethoxycarbonyl (also known as Fmoc).

Among the radicals R3, mention may be made of methyl, ethyl, propyl, benzyl, ethylhexyl, lauryl, stearyl and behenyl (—(CH$_2$)$_{21}$—CH$_3$) chains, and also fluoroalkyl chains, for instance heptadecafluorooctylsulfonyl-aminoethyl CF$_3$—(CF$_2$)$_7$—SO$_2$—N(C$_2$H$_5$)—CH$_2$—CH$_2$; or alternatively —CH$_2$—CH$_2$—CN, succinimido, maleimido, mesityl, tosyl, triethoxysilane or phthalimide chains.

The amine units and/or the anionic groups of monomer of formula (I) may optionally be neutralized, especially in the manner described later.

Among the monomers of formula (I) that are particularly preferred, mention may be made of:

poly(ethylene glycol) (meth)acrylate in which R1 is H or methyl; Z is COO, x=1, m=0 and R3=H;

methylpoly(ethylene glycol) (meth)acrylate, also known as methoxypoly(ethylene glycol) (meth)acrylate, in which R1 is H or methyl, Z is COO, x=1, m=0 and R3=methyl;

alkylpoly(ethylene glycol) (meth)acrylates in which R1 is H or methyl, Z is COO, x=1, m=0 and R3=alkyl;

phenylpoly(ethylene glycol) (meth)acrylate, also known as poly(ethylene glycol)phenyl ether(meth)acrylate, in which R1 is H or methyl, Z is COO, x=1, m=0 and R3=phenyl;

the following monomer:

in which n is preferably between 3 and 100 inclusive and especially 5 to 50 inclusive, or even 7 to 30 inclusive.

The monomers of formula (I) that are most particularly preferred are chosen from poly(ethylene glycol) (meth)acrylates and methylpoly(ethylene glycol) (meth)acrylates, preferably those with a molecular weight of between 350 and 13 000 g/mol and especially between 500 and 8000 g/mol.

Poly(ethylene glycol) (meth)acrylates are most particularly preferred, and in particular those with a molecular weight of between 350 and 13 000 g/mol and especially between 500 and 8000 g/mol.

Examples of commercial monomers are:

CD 350 (methoxypoly(ethylene glycol 350) methacrylate) and CD 550 (methoxypoly(ethylene glycol 550) methacrylate), sold by Sartomer Chemicals;

M90G (methoxypolyethylene glycol methacrylate (9 repeating units)) and M230G (methoxypolyethylene glycol methacrylate (23 repeating units)) available from Shin-Nakamura Chemicals;

methoxypoly(ethylene glycol)methacrylates with average molecular weights of 300, 475 or 1100, available from Sigma-Aldrich;

methoxypoly(ethylene glycol)acrylate with an average molecular weight of 426, available from Sigma-Aldrich;

methoxypoly(ethylene glycol)methacrylates available from Laporte under the trade names: MPEG 350, MPEG 550, S10W, S20W;

poly(ethylene glycol) monomethyl ether, mono(succinimidyl succinate) ester with an average molecular weight of 1900 or 5000, from Polysciences;

behenylpoly(ethylene glycol PEG-25) methacrylate, available from Rhodia under the name Sipomer BEM;

poly(ethylene glycol)phenyl ether acrylates with average molecular weights of 236, 280 or 324, available from Aldrich;

methoxypolyethylene glycol 5000 2-(vinylsulfonyl)ethyl ether available commercially from Fluka;

polyethylene glycol ethyl ether methacrylate available from Aldrich;

polyethylene glycol 8000, 4000, 2000 methacrylates from Monomer & Polymer Dajac Laboratories;

polyethylene glycol N-hydroxysuccinimide, vinyl sulfone available commercially from Nektar Molecule Engineering (Shearwater).

Preferably, the monomer of formula (I) has a molecular weight of between 350 and 13 000 g/mol and especially between 500 and 8000 g/mol.

The monomer of formula (I), alone or as a mixture, is present in a proportion of from 10% inclusive to 60% exclusive by weight, especially from 20% inclusive to 55% inclusive by weight and preferably from 30% inclusive to 50% inclusive by weight relative to the weight of the final polymer.

The ethylenic copolymer according to the invention also comprises at least one "essentially cationic" monomer, and/or a salt thereof, chosen from:

(i) one or more cationic monomers of formula (IIa),
(ii) one or more amphoteric monomers of formulae (IIc) and (IId), and
(iii) a mixture of one or more cationic monomers of formula (IIa) with one or more anionic monomers chosen from maleic anhydride and/or those of formula (IIb); and/or with one or more amphoteric monomers chosen from those of formulae (IIc) and (IId).

Preferably, the "essentially cationic" monomer is chosen from the cationic monomers of formula (IIa) and the amphoteric monomers of formula (IIc) or (IId), preferentially from the cationic monomers of formula (IIa).

The term "cationic monomer" means a monomer comprising units capable of bearing a cationic charge in the pH range of between 3 and 12. These units do not necessarily have a permanent charge irrespective of the pH. The cationic unit does not need to be protonated at each of these pH values.

$$H_2C=C\begin{matrix}R_1\\ \\(Z')_{x'}-(R_2')_{m'}-X\end{matrix} \quad (IIa)$$

$$H_2C=C\begin{matrix}R_1\\ \\(Z')_{x'}-(R_2')_{m'}-Y\end{matrix} \quad (IIb)$$

$$H_2C=C\begin{matrix}R_1\\ \\(Z')_{x'}-(R_2')_{m'}-X'^{+}-(R'_3)_{n'}-Y'^{-}\end{matrix} \quad (IIc)$$

$$H_2C=C\begin{matrix}R_1\\ \\(Z')_{x'}-(R_2')_{m'}-O-\overset{O}{\underset{O}{P^{-}}}-O-(R'_3)_{n'}-X''^{+}\end{matrix} \quad (IId)$$

in which:

R1 is a hydrogen atom or a linear or branched hydrocarbon-based radical of the type $C_pH_{2p+1}$, with p being an integer between 1 and 12 inclusive.

R1 may especially represent a methyl, ethyl, propyl, or butyl radical. Preferably, R1 represents hydrogen or a methyl radical.

Z' is a divalent group chosen from —COO—, —CONH—, —CONCH₃—, —OCO— or —O—, —SO₂— —CO—O—CO— or —CO—CH₂—CO—.

Preferably, Z' is chosen from COO and CONH.

x' is 0 or 1, preferably 1.

R'2 is a saturated or unsaturated, optionally aromatic, linear, branched or cyclic divalent carbon-based radical of 1 to 30 carbon atoms, possibly comprising 1 to 18 heteroatoms chosen from O, N, S, F, Si and P.

In the radical R'2, the heteroatom(s), when they are present, may be intercalated in the chain of said radical R'2, or alternatively said radical R'2 may be substituted with one or more groups comprising them such as hydroxyl or amino (NH2, NHR' or NR'R" with R' and R", which may be identical or different, representing a linear or branched C1-C22 alkyl, especially methyl or ethyl).

R'2 may especially be:

an alkylene radical such as methylene, ethylene, propylene, n-butylene, isobutylene, tert-butylene, n-hexylene, n-octylene, n-dodecylene, n-octadecylene, n-tetradecylene or n-docosanylene;

a phenylene radical —C$_6$H$_4$— (ortho, meta or para), optionally substituted with a C1-C12 alkyl radical optionally comprising 1 to 25 heteroatoms chosen from N, O, S, F, Si and/or P; or alternatively a benzylene radical —C$_6$H$_4$—CH$_2$—, optionally substituted with a C1-C12 alkyl radical optionally comprising 1 to 25 heteroatoms chosen from O, N, S, F, Si and P;

a radical of formula —CH$_2$—O—CO—O—, —CH$_2$—CH$_2$—O—CO—O—, —CH$_2$—CO—O—, —CH$_2$—CH$_2$—CO—O—, —[(CH$_2$)$_5$—CO—O]$_n$—, —CH$_2$—CH(CH$_3$)—O—, —(CH$_2$)$_2$—O—, —CH$_2$—O—CO—NH—, —CH$_2$—CH$_2$—O—CO—NH—; —CH$_2$—NH—CO—NH— or —CH$_2$—CH$_2$—NH—CO—NH—, —CH$_2$—CHOH—, —CH$_2$—CH$_2$—CHOH—, —CH$_2$—CH$_2$—CH(NH$_2$)—, —CH$_2$—CH(NH$_2$)—, —CH$_2$—CH$_2$—CH(NHR')—, —CH$_2$—CH(NHR')—, —CH$_2$—CH$_2$—CH(NR'R")—, —CH$_2$—CH(NR'R")—, —CH$_2$—CH$_2$—CH$_2$—NR'—, —CH$_2$—CH$_2$—CH$_2$—O—; —CH$_2$—CH$_2$—CHR'—O— with R' and R" representing a linear or branched C1-C22 alkyl optionally comprising 1 to 12 heteroatoms chosen from O, N, S, F, Si and P;

or a mixture of these radicals;

m' is 0 or 1;

X (in formula IIa) is a guanidino or amidino group, or a group of formula —N(R$_6$)(R$_7$) or —P(R$_6$)(R$_7$) or —P$^+$R$_6$R$_7$R$_8$, with R6, R7 and R8 representing, independently of each other, either (i) a hydrogen atom, or (ii) a linear, branched or cyclic, saturated or unsaturated, optionally aromatic alkyl group containing from 1 to 18 carbon atoms, possibly comprising 1 to 10 heteroatoms chosen from O, N, S, F, Si and P; or (iii) R6 and R7 may form with the nitrogen or phosphorus atom a first saturated or unsaturated, optionally aromatic ring comprising in total 5, 6, 7 or 8 atoms, and especially 4, 5 or 6 carbon atoms and/or 2 to 4 heteroatoms chosen from O, S and N; said first ring possibly being fused with one or more other saturated or unsaturated, optionally aromatic rings each comprising 5, 6 or 7 atoms, and especially 4, 5, 6 or 7 carbon atoms and/or 2 to 4 heteroatoms chosen from O, S and N.

For example, R6 and R7 may be chosen from hydrogen and a methyl, ethyl, propyl, isopropyl, n-butyl, t-butyl, isobutyl, octyl, lauryl or stearyl group.

Preferably, R6 and R7 are chosen, independently of each other, from H, CH3 and C2H5.

Alternatively, X may represent a group —R'6-N—R'7- in which R'6 and R'7 form with the nitrogen atom a saturated or unsaturated, optionally aromatic ring comprising in total 5, 6, 7 or 8 atoms, and especially 4, 5 or 6 carbon atoms and/or 2 to 4 heteroatoms chosen from O, S and N; said ring possibly being fused with one or more other saturated or unsaturated, optionally aromatic rings, each comprising 5, 6 or 7 atoms, and especially 4, 5, 6, 7 or 8 carbon atoms and/or 2 to 4 heteroatoms chosen from O, S and N.

For example, X may constitute an aromatic or nonaromatic ring comprising a tertiary amine group or may represent an aromatic or nonaromatic heterocycle containing a tertiary nitrogen.

Among these preferred radicals X, mention may be made of radicals of pyridine, indolyl, isoindolinyl, imidazolyl, imidazolinyl, piperidyl, pyrazolinyl, pyrazolyl, quinoline, pyrazolinyl, pyridyl, piperazinyl, pyrrolidinyl, quinidinyl, thiazolinyl, morpholine, guanidino or amidino type, and mixtures thereof.

The guanidino and amidino groups are, respectively, of formula:

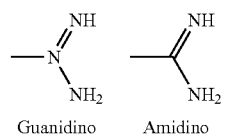

Guanidino    Amidino

The monomers of formula (IIa) may be neutralized by neutralizers of different chemical nature, in the manner described later.

Among the preferred monomers of formula (IIa) that may be mentioned are:

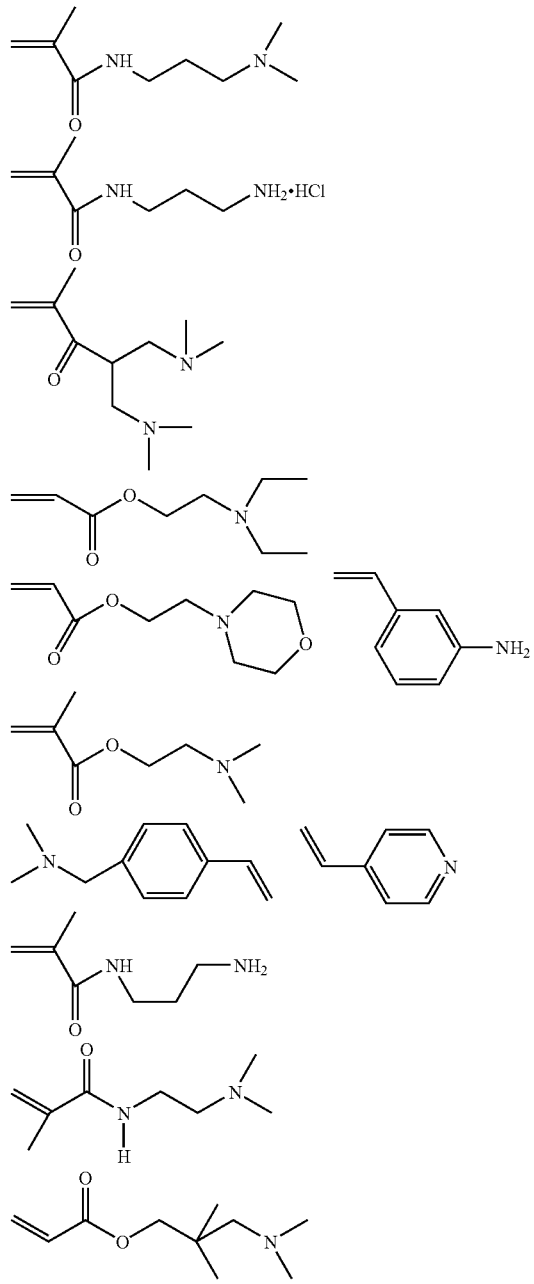

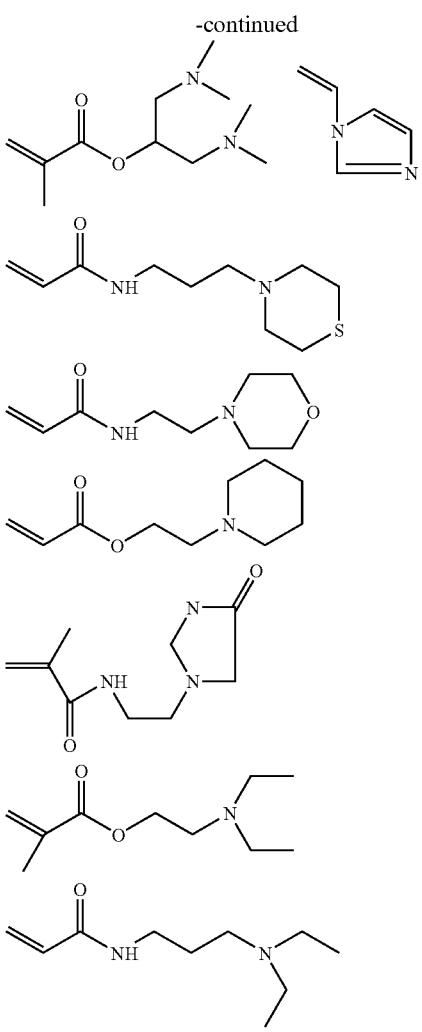

Among the monomers of formula (IIa) that are particularly preferred, mention may be made of dimethylaminopropyl (meth)acrylamide, dimethylamino-ethyl(meth)acrylamide, diethylaminoethyl(meth)acrylate, dimethylaminoethyl (meth)acrylate, vinylimidazole, vinylpyridine and morpholinoethyl(meth)acrylate.

In formula (IIb), the meaning of the radicals R1, Z', X', R'2 and m' is the same as that given above for formula (IIa).

In formula (IIb), Y is a group chosen from —COOH, —SO$_3$H, —OSO$_3$H, —PO$_3$H$_2$ and —OPO$_3$H$_2$.

It is understood that, according to the prior art, the groups SO$_4$H$_2$ and PO$_3$H are linked to R'2 via the S and P atoms, respectively.

The anionic groups of the monomers of formula (IIb) may optionally be neutralized, especially in the manner described later.

Among the anionic monomers that are preferred, mention may be made of maleic anhydride and the following preferred monomers of formula (IIb): acrylic acid, methacrylic acid, crotonic acid, itaconic acid, fumaric acid, maleic acid, 2-carboxyethyl acrylate (CH2=CH—C(O)—O—(CH$_2$)$_2$—COOH); styrenesulfonic acid, 2-acrylamido-2-methylpropanesulfonic acid, vinylbenzoic acid, vinylphosphoric acid and sulfopropyl(meth)-acrylate, and salts thereof.

In formula (IIc), the meaning of the radicals R1, Z', X', R'2 and m' is the same as that given above for formula (IIa).

The other radicals have the following meaning:

X'$^+$ is a divalent group of formula —N$^+$(R$_6$)(R$_7$)— with R6 and R7 representing, independently of each other, either (i) a hydrogen atom, or (ii) a linear, branched or cyclic, optionally aromatic alkyl group containing from 1 to 25 carbon atoms, possibly comprising 1 to 20 heteroatoms chosen from O, N, S and P; or (iii) R6 and R7 may form with the nitrogen atom a first saturated or unsaturated, optionally aromatic ring comprising in total 5, 6, 7 or 8 atoms, and especially 4, 5, 6 or 7 carbon atoms and/or 2 to 3 heteroatoms chosen from O, S and N; said first ring possibly being fused with one or more other saturated or unsaturated, optionally aromatic rings, each comprising 5, 6, 7 or 8 atoms, and especially 4, 5, 6 or 7 carbon atoms and/or 2 to 3 heteroatoms chosen from O, S and N.

For example, R6 and R7 may be chosen from hydrogen and a methyl, ethyl, propyl, isopropyl, n-butyl, t-butyl or isobutyl group.

Among the preferred radicals X'$^+$ that may be mentioned are radicals of pyridine, indolyl, isoindolinyl, imidazolyl, imidazolinyl, piperidyl, pyrazolinyl, pyrazolyl, quinoline, pyrazolinyl, pyridyl, piperazinyl, pyrrolidinyl, quinidinyl, thiazolinyl, morpholine, guanidino or amidino type, and mixtures thereof.

Y'$^-$ is a group chosen from —COO$^-$, —SO$_3^-$, —OSO$_3^-$, —PO$_3^{2-}$ and —OPO$_3^{2-}$.

R'3 is a saturated or unsaturated, optionally aromatic, linear, branched or cyclic divalent carbon-based radical of 1 to 30 carbon atoms, possibly comprising 1 to 18 heteroatoms chosen from O, N, S, F, Si and P.

In the radical R'3, the heteroatom(s), when they are present, may be intercalated in the chain of said radical R'3, or alternatively said radical R'3 may be substituted with one or more groups comprising them such as hydroxyl or amino (NH$_2$, NHR' or NR'R" with R' and R", which may be identical or different, representing a linear or branched C1-C18 alkyl, especially methyl or ethyl).

R'3 may especially be:

an alkylene radical such as methylene, ethylene, propylene, n-butylene, isobutylene, tert-butylene, n-hexylene, n-octylene, n-dodecylene, n-octadecylene, n-tetradecylene or n-docosanylene;

a phenylene radical —C$_6$H$_4$— (ortho, meta or para) optionally substituted with a C1-C12 alkyl radical optionally comprising 1 to 5 heteroatoms chosen from O, N, S, F, Si and P; or alternatively a benzylene radical —C$_6$H$_4$—CH$_2$—, optionally substituted with a C1-C12 alkyl radical optionally comprising 1 to 5 heteroatoms chosen from O, N, S, F, Si and P;

a radical of formula —CH$_2$—O—CO—O—, CH$_2$—CH$_2$—O—CO—O—, —CH$_2$—CO—O—, —CH$_2$—CH$_2$—CO—O—, —[(CH$_2$)$_5$—CO—O]$_n$—, —CH$_2$—CH(CH$_3$)—O—, —(CH$_2$)$_2$—O—, —CH$_2$—O—CO—NH—, —CH$_2$—CH$_2$—O—CO—NH—; —CH$_2$—NH—CO—NH— or —CH$_2$—CH$_2$—NH—CO—NH—, —CH$_2$—CHOH—, —CH$_2$—CH$_2$—CHOH—, —CH$_2$—CH$_2$—CH(NH$_2$)—, —CH$_2$—CH(NH$_2$)—, —CH$_2$—CH$_2$—CH(NHR')—, —CH$_2$—CH(NHR')—, —CH$_2$—CH$_2$—CH(NR'R")—, —CH$_2$—CH(NR'R")—, —CH$_2$—CH$_2$—CH$_2$—NR'—, —CH$_2$—CH$_2$—CH$_2$—O—; —[CH$_2$—CH$_2$—O]$_n$— and —[CH$_2$—CH(CH$_3$)—O]$_n$—, —CH$_2$—CH$_2$—CHR'—O— with R' and R" representing a linear or branched C1-C22 alkyl optionally comprising 1 to 12 heteroatoms chosen from O, N, S, F, Si and P;

or a mixture of these radicals;

n' is between 1 and 100 and preferably between 1 and 5 inclusive.

In formula (IId), the meaning of the radicals R1, Z', X', R'2 and m' is the same as that given above for formula (IIa), and that of the radicals R'3 and n' is the same as that given for formula (IIc).

In formula (IId), $X''^+$ is a group of formula —$N^+R_6R_7R_8$ with R6, R7 and R8 representing, independently of each other, either (i) a hydrogen atom, or (ii) a linear, branched or cyclic, optionally aromatic alkyl group containing from 1 to 18 carbon atoms, possibly comprising 1 to 5 heteroatoms chosen from O, N, S and P; or (iii) R6 and R7 may form with the nitrogen atom a first saturated or unsaturated, optionally aromatic ring comprising in total 5, 6 or 7 atoms, and especially 4, 5 or 6 carbon atoms and/or 2 to 3 heteroatoms chosen from O, S and N; said first ring possibly being fused with one or more other saturated or unsaturated, optionally aromatic rings, each comprising 5, 6 or 7 atoms, and especially 4, 5, 6 or 7 carbon atoms and/or 2 to 3 heteroatoms chosen from O, S and N.

For example, R6, R7 and R8 may be chosen from hydrogen and a methyl, ethyl, propyl, isopropyl, n-butyl, t-butyl, isobutyl, octyl, lauryl or stearyl group.

Among the preferred radicals $X''^+$ that may be mentioned are trimethylammonium; triethylammonium; N,N-di-methyl-N-octylammonium; N,N-dimethyl-N-laurylammonium radicals.

Among the preferred monomers of formula (IIc) or (IId) that may be mentioned are N,N-dimethyl-N-(2-methacryloyloxyethyl)-N-(3-sulfopropyl)ammonium betaine (especially SPE from the company Raschig); N,N-dimethyl-N-(3-methacrylamidopropyl)-N-(3-sulfopropyl)-ammonium betaine (SPP from Raschig) and 1-(3-sulfopropyl)-2-vinylpyridinium betaine (SPV from Raschig), and also 2-methacryloyloxyethylphosphoryl-choline.

When the "essentially cationic" monomer is chosen from mixtures of cationic and/or amphoteric monomers with anionic monomers, said anionic monomers are preferably present in a proportion of from 5% to 40% by weight, especially from 10% to 30% by weight and preferably from 15% to 25% by weight relative to the weight of the "cationic and/or amphoteric+anionic monomers" mixture.

The "essentially cationic" monomer is present in a proportion of from 40% exclusive to 90% inclusive, especially from 45% inclusive to 80% inclusive and preferably from 50% inclusive to 70% inclusive by weight relative to the weight of the final polymer.

The ethylenic polymer consists essentially of monomer(s) of formula (I) and of essentially cationic monomer(s), according to the invention, which means that it optionally does not comprise monomers other than those mentioned above.

Preferably, the polymer according to the invention comprises the monomers of formula (I) and the "essentially cationic" monomers in a weight ratio that may range from 60/40 to 40/60, with a preference for a 50/50 ratio.

It is thus possible to neutralize one and/or the other of the above monomers before polymerization, or alternatively to neutralize the polymer once formed. Preferably, the polymer is neutralized after it has been formed.

The neutralization of the anionic groups, whether they belong to the polymer and/or to the monomers, especially those of formula (I) and/or (IIb), may be performed with a mineral base, such as LiOH, NaOH, KOH, Ca(OH)$_2$, NH$_4$OH, Mg(OH)$_2$ or Zn(OH)$_2$; or with an organic base such as a primary, secondary or tertiary alkylamine, especially triethylamine or butylamine. This primary, secondary or tertiary alkylamine may comprise one or more nitrogen and/or oxygen atoms and may thus comprise, for example, one or more alcohol functions; mention may be made especially of 2-amino-2-methylpropanol, triethanolamine and 2-dimethylamino-propanol. Mention may also be made of lysine or 3-(dimethylamine)propylamine.

Neutralization of the amine units, belonging to the polymer and/or to the monomers, especially those of formula (I) and/or (IIa), may be performed with a mineral acid, such as sulfuric acid, hydrochloric acid, hydrobromic acid, hydriodic acid, phosphoric acid or boric acid; or with an organic acid, which may comprise one or more carboxylic, sulfonic or phosphonic acid groups. They may be linear, branched or cyclic aliphatic acids, or alternatively unsaturated or aromatic acids. These acids may also comprise one or more heteroatoms chosen from O, N, Si, F and P, for example in the form of hydroxyl groups. Mention may be made especially of propionic acid, acetic acid, terephthalic acid, citric acid and tartaric acid; betaine HCl or betaine hydrochloride of formula (CH$_3$)$_3$N+CH$_2$CO$_2$H.Cl—; gluconic acid, 2-ethylcaproic acid, oleic acid, behenic acid and stearic acid.

Advantageously, the neutralizer for the amine units may be chosen, alone or as a mixture, from neutralizers of mineral or organic acid type, with a log P value of less than or equal to 2, for example between −8 and 2, preferably between −6 and 1 and especially between −6 and 0.

It may also be chosen, alone or as a mixture, from mineral or organic acid neutralizers with a log P value of greater than 2, preferably greater than or equal to 2.5, especially greater than 3 and in particular between 3 and 15, or even 3.5 and 10.

Preferentially, it is chosen from neutralizers of mineral or organic acid type with a log P value of less than or equal to 2, for example between −8 and 2, preferably between −6 and 1 and especially between −6 and 0.

The log P values are known and determined according to a standard test that determines the concentration of the compound in 1-octanol and water.

The values may especially be calculated using the ACD software (Advanced Chemistry Development) software Solaris V4.67; they may also be obtained from Exploring QSAR: hydrophobic, electronic and stearic constants (ACS professional reference book, 1995). A website also exists that provides estimated values (address: http://esc.syrres.com/interkow/kowdemo.htm).

The log P value of certain common acids is given below for information purposes:

| | |
|---|---|
| Sulfuric acid | −1.031 +/− 0.613 |
| Acetic acid | −0.285 +/− 0.184 |
| Propionic acid | 0.246 +/− 0.184 |
| Citric acid | −1.721 +/− 0.396 |
| Gluconic acid | −3.175 +/− 0.852 |
| Boric acid | −0.292 +/− 0.753 |
| Phosphoric acid | −2.148 +/− 0.587 |
| Benzoic acid | 1.895 +/− 0.206 |
| Stearic acid | 8.216 +/− 0.186 |
| Behenic acid | 10.342 +/− 0.186 |
| Oleic acid | 7.698 +/− 0.199 |

2-Ethylcaproic acid, oleic acid, behenic acid, stearic acid, acetic acid, citric acid, tartaric acid, betaine hydrochloride and/or gluconic acid may preferably be used as neutralizer, and preferentially betaine hydrochloride and/or behenic acid.

Preferably, the polymer according to the invention is such that:

the monomer of formula (I), alone or as a mixture, is present in a proportion of from 10% inclusive to 60% exclusive by weight, especially from 20% inclusive to 55% inclusive by weight, preferably from 30% inclusive to 50% inclusive by weight, relative to the weight of the final polymer, and is chosen, alone or as a mixture, from poly(ethylene glycol) (meth)acrylates and/or methylpoly(ethylene glycol) (meth) acrylates, preferably those with a molecular weight of between 350 and 13 000 g/mol and especially between 500 and 8000 g/mol; and/or the "essentially cationic" monomer is present in a proportion of from 40% exclusive to 90% inclusive by weight, especially from 45% inclusive to 80% inclusive by weight and preferably from 50% inclusive to 70% inclusive by weight relative to the weight of the final polymer, and is chosen, alone or as a mixture, from the monomers of formula (IIb).

The polymers that are most particularly preferred are those in which:

the monomer of formula (I), alone or as a mixture, is present in a proportion of from 10% inclusive to 60% exclusive by weight, especially from 20% inclusive to 55% inclusive by weight and preferably from 30% inclusive to 50% inclusive by weight, relative to the weight of the final polymer, and is chosen, alone or as a mixture, from poly(ethylene glycol) (meth)acrylates, preferably those with a molecular weight of between 350 and 13 000 g/mol and especially between 500 and 8000 g/mol; and the "essentially cationic" monomer is present in a proportion of from 40% exclusive to 90% inclusive by weight, especially from 45% exclusive to 80% inclusive by weight and preferably from 50% inclusive to 70% inclusive by weight relative to the weight of the final polymer, and is chosen, alone or as a mixture, from dimethylaminopropyl (meth)acrylamide, dimethyl-aminoethyl(meth)acrylamide, diethylaminoethyl(meth)acrylate, dimethylaminoethyl (meth)acrylate, vinylimidazole, vinylpyridine and morpholinoethyl(meth)acrylate; and also preferably:

the polymer is neutralized with a neutralizer chosen from 2-ethylcaproic acid, oleic acid, behenic acid, stearic acid, acetic acid, citric acid, tartaric acid, betaine hydrochloride and/or gluconic acid, and preferentially behenic acid and/or betaine hydro-chloride.

The polymers that are even more particularly preferred are those in which:

the monomer of formula (I), alone or as a mixture, is present in a proportion of from 10% inclusive to 60% exclusive by weight, especially from 20% inclusive to 55% inclusive by weight and preferably from 30% inclusive to 50% inclusive by weight, relative to the weight of the final polymer, and is chosen, alone or as a mixture, from poly(ethylene glycol) (meth)acrylates, preferably those with a molecular weight of between 350 and 13 000 g/mol and especially between 500 and 8000 g/mol; and the "essentially cationic" monomer is present in a proportion of from 40% exclusive to 90% inclusive by weight, especially from 45% inclusive to 80% inclusive by weight and preferably from 50% inclusive to 70% inclusive by weight, relative to the weight of the final polymer, and is chosen, alone or as a mixture, from dimethylaminopropyl (meth)acrylamide, and the polymer is neutralized with a neutralizer chosen from behenic acid and/or betaine hydrochloride.

The polymers according to the invention may be prepared according to the usual standard radical polymerization methods known to those skilled in the art, and as described, for example, in the book "Chimie et physicochimie des polymères" by Gnanou et al. (published by Dunod).

These polymers may especially be prepared by:

direct solution polymerization in water with optional preneutralization of the cationic unit and/or of the anionic unit;

emulsion polymerization in water with optional preneutralization of the cationic unit and/or of the anionic unit with use of a surfactant;

polymerization in an organic solvent, such as ethanol or methyl ethyl ketone, with optional preneutralization of the cationic unit and/or of the anionic unit, followed by a step of dissolution or dispersion in water with evaporation of the solvent.

These polymerizations may be performed in the presence of a radical initiator especially of peroxide type (Trigonox 21S: tert-butyl peroxy-2-ethylhexanoate) or azo type (AIBN V50: 2,2'-azobis(2-amidinopropane)dihydrochloride) or potassium ammonium persulfate, which may be present in a proportion of from 0.3% to 5% by weight relative to the total weight of the monomers.

The polymers according to the invention are non-crosslinked. They are in the form of statistical, preferably film-forming, ethylenic copolymers of one more ethylenic monomers containing PEG groups (the PEG groups are pendent along the backbone) and of one or more ethylenic monomers comprising cationic functions (nonquaternary neutralized amines) and/or betaine functions, which are preferably monovalent.

The term "ethylenic" polymer means a polymer obtained by polymerization of ethylenically unsaturated monomers.

The term "film-forming" polymer means a polymer that can form, by itself or in the presence of an auxiliary film-forming agent, a continuous film that adheres to a support, especially to keratin materials.

The copolymers according to the invention have a weight-average molecular mass (Mw) that is preferably between 500 and 5 000 000, especially between 1000 and 3 000 000 and more preferentially between 2000 and 2 000 000, or even between 4000 and 500 000, inter alia between 7000 and 400 000, even better between 20 000 and 350 000 and better still between 150 000 and 300 000.

The weight-average molar masses (Mw) are determined by gel permeation chromatography or by light scattering, depending on the accessibility of the method (solubility of the polymers under consideration).

The polymers according to the invention may preferably be conveyed in aqueous medium, i.e. they are preferably water-soluble or water-dispersible.

The dissolution or dispersion in water may be performed by direct dissolution of the polymer if it is soluble, or alternatively by neutralization of the amine units and/or acid units so as to make the polymer soluble or dispersible in water.

The dissolution or dispersion in water may also be performed via an intermediate step of dissolution in an organic solvent followed by the addition of water before evaporation of the organic solvent.

Moreover, it has been found that the polymers according to the invention advantageously have a viscosity in water that is adequate for the envisioned applications, which may be, for example, between 1 and 1000 mPa·s, preferably between 1.5 and 750 mPa·s and better still between 2 and 500 mPa·s.

The viscosity is measured using a Brookfield viscometer, for a solution containing 15% by weight of polymer in water or methyl ethyl ketone (solvent chosen as a function of the solubility of the polymer and/or of the polymerization method), at 25° C., with a needle-type spindle chosen from the model numbers 00 to 07 from Brookfield, preferably a No. 1 spindle; for a measuring time of 5 minutes, at a speed of between 0.1 and 6 rpm. The viscosity is measured after total dissolution of the polymer in water or methyl ethyl ketone.

In addition, the polymers according to the invention may preferably have a glass transition temperature (Tg) of between −150° C. and 20° C., especially −120° C. and 10° C. and better still between −100° C. and 0° C.; the Tg is measured according to the method given before the examples.

The polymers according to the invention may preferably have a melting point (m.p.) of between −100° C. and 80° C., especially between −80° C. and 50° C. and better still between −70° C. and 45° C., or even between −10° C. and 25° C.

In addition, the polymers according to the invention preferably have a water uptake of between 3% and 150% by weight, preferably between 4% and 100% by weight and especially between 5% and 50% by weight, at 75% relative humidity (75% RH); the water uptake is measured according to the method given before the examples.

They may also have a water uptake of between 3% and 200% by weight, preferably between 2.5% and 150% by weight and especially between 3% and 100% by weight, at 85% relative humidity (85% RH).

The polymers according to the invention find a most particular application in the field of cosmetics. They may be present in the composition in dissolved form, for example in water or an organic solvent, or alternatively in the form of an aqueous or organic dispersion.

They may be used in the cosmetic or pharmaceutical compositions according to the invention in a proportion of from 0.01% to 50% by weight of solids, especially from 0.1% to 30% by weight or even from 0.3% to 10% by weight and better still from 1% to 3% by weight relative to the total weight of the composition.

The cosmetic or pharmaceutical compositions according to the invention comprise, besides said polymers, a physiologically acceptable medium, especially a cosmetically, dermatologically or pharmaceutically acceptable medium, i.e. a medium that is compatible with keratin materials such as facial or bodily skin, the hair, the eyelashes, the eyebrows and the nails.

The composition may thus comprise a hydrophilic medium comprising water or a mixture of water and hydrophilic organic solvent(s), for instance alcohols and especially linear or branched C1-C6 monoalcohols, for instance ethanol, isopropanol or n-propanol, and polyols, for instance glycerol, diglycerol, propylene glycol, sorbitol or pentylene glycol, and polyethylene glycols, or alternatively hydrophilic C2 ethers and $C_2$-$C_4$ aldehydes.

The water or the mixture of water and hydrophilic organic solvents may be present in the composition according to the invention in a content ranging from 0.1% to 99% by weight and preferably from 10% to 80% by weight relative to the total weight of the composition.

The composition may also comprise a fatty phase, which may comprise fatty substances that are liquid at room temperature (in general 25° C.) and/or fatty substances that are solid at room temperature, such as waxes, pasty fatty substances and gums, and mixtures thereof. These fatty substances may be of animal, plant, mineral or synthetic origin. This fatty phase may also contain lipophilic organic solvents.

As fatty substances that are liquid at room temperature, often referred to as oils, which may be used in the invention, mention may be made of: hydrocarbon-based oils of animal origin such as perhydrosqualene; hydrocarbon-based plant oils such as liquid triglycerides of fatty acids of 4 to 10 carbon atoms, for instance heptanoic or octanoic acid triglycerides, or alternatively sunflower oil, maize oil, soybean oil, grapeseed oil, sesame seed oil, apricot oil, macadamia oil, castor oil, avocado oil, caprylic/capric acid triglycerides, jojoba oil, shea butter, linear or branched hydrocarbons of mineral or synthetic origin, such as liquid paraffin and derivatives thereof, petroleum jelly, polydecenes, hydrogenated polyisobutene such as parleam; synthetic esters and ethers, especially of fatty acids, for instance purcellin oil, isopropyl myristate, 2-ethyl-hexyl palmitate, 2-octyldodecyl stearate, 2-octyl-dodecyl erucate, isostearyl isostearate; hydroxylated esters, for instance isostearyl lactate, octyl hydroxy-stearate, octyldodecyl hydroxystearate, diisostearyl malate, triisocetyl citrate, and fatty alcohol heptanoates, octanoates and decanoates; polyol esters, for instance propylene glycol dioctanoate, neopentyl glycol diheptanoate and diethylene glycol diisononanoate; and pentaerythritol esters; fatty alcohols containing from 12 to 26 carbon atoms, for instance octyldodecanol, 2-butyloctanol, 2-hexyl-decanol, 2-undecylpentadecanol and oleyl alcohol; partially hydrocarbon-based fluoro oils and/or partially silicone-based fluoro oils; silicone oils, for instance volatile or non-volatile, linear or cyclic polymethylsiloxanes (PDMSs), which are liquid or pasty at room temperature, for instance cyclomethicones, dimethicones, optionally comprising a phenyl group, for instance phenyl trimethicones, phenyltrimethylsiloxy-diphenylsiloxanes, diphenylmethyldimethyltrisiloxanes, diphenyl dimethicones, phenyl dimethicones and polymethylphenylsiloxanes; mixtures thereof.

These oils may be present in a content ranging from 0.01% to 90% and better still from 0.1% to 85% by weight relative to the total weight of the composition.

The composition according to the invention may also comprise one or more physiologically acceptable organic solvents.

These solvents may be generally present in a content ranging from 0.1% to 90%, preferably from 0.5% to 85%, more preferably from 10% to 80% and better still from 30% to 50% by weight, relative to the total weight of the composition.

Mention may be made especially, besides the hydrophilic organic solvents mentioned above, of ketones that are liquid at room temperature such as methyl ethyl ketone, methyl isobutyl ketone, diisobutyl ketone, isophorone, cyclohexanone and acetone; propylene glycol ethers that are liquid at room temperature, such as propylene glycol monomethyl ether, propylene glycol monomethyl ether acetate, and dipropylene glycol mono-n-butyl ether; short-chain esters (containing from 3 to 8 carbon atoms in total), such as ethyl acetate, methyl acetate, propyl acetate, n-butyl acetate and isopentyl acetate; ethers that are liquid at 25° C., such as diethyl ether, dimethyl ether or dichlorodiethyl ether; alkanes that are liquid at 25° C., such as decane, heptane, dodecane, isododecane and cyclohexane; aromatic cyclic compounds that are liquid at 25° C., such as toluene and xylene; aldehydes that are liquid at 25° C., such as benzaldehyde and acetaldehyde, and mixtures thereof.

For the purposes of the present invention, the term "wax" means a lipophilic compound that is solid at room temperature (25° C.), which undergoes a reversible solid/liquid change of state, and which has a melting point of greater than or equal to 25° C., which may be up to 120° C. By bringing the wax to the liquid state (melting), it is possible to make it miscible with the oils possibly present and to form a microscopically homogeneous mixture, but, on returning the temperature of the mixture to room temperature, recrystallization of the wax is obtained in the oils of the mixture. The melting point of the wax may be measured using a differential scanning calorimeter (DSC), for example the calorimeter sold under the name DSC 30 by the company Mettler.

The waxes may be hydrocarbon-based waxes, fluoro waxes and/or silicone waxes and may be of plant, mineral, animal and/or synthetic origin. In particular, the waxes have a melting point of greater than 30° C. and better still greater than 45° C. As waxes that may be used in the composition of the invention, mention may be made of beeswax, carnauba wax or candelilla wax, paraffin, microcrystalline waxes, ceresin or ozokerite, synthetic waxes, for instance polyethylene waxes or Fischer-Tropsch waxes, and silicone waxes, for instance alkyl or alkoxy dimethicones containing from 16 to 45 carbon atoms.

The gums are generally polydimethylsiloxanes (PDMSs) of high molecular weight or cellulose gums or polysaccharides, and the pasty substances are generally hydrocarbon-based compounds, for instance lanolins and derivatives thereof, or PDMSs.

The nature and amount of the solid substances depend on the desired mechanical properties and textures. As a guide, the composition may contain from 0.1% to 50% by weight and better still from 1% to 30% by weight of waxes relative to the total weight of the composition.

The composition according to the invention may also comprise, in a particulate phase, pigments and/or nacres and/or fillers usually used in cosmetic compositions.

The composition may also comprise other dyestuffs chosen from water-soluble dyes and/or liposoluble dyes that are well known to those skilled in the art.

The term "pigments" should be understood as meaning white or colored, mineral or organic particles of any shape, which are insoluble in the physiological medium and which are intended to color the composition.

The term "fillers" should be understood as meaning colorless or white, mineral or synthetic, lamellar or non-lamellar particles intended to give body or rigidity to the composition, and/or softness, a matt effect and uniformity to the makeup result.

The term "nacres" should be understood as meaning iridescent particles of any form, produced especially by certain molluscs in their shell, or else synthesized.

The pigments may be present in the composition in a proportion of from 0.01% to 25% and preferably in a proportion of from 3% to 10% by weight of the final composition. They may be white or colored, and mineral or organic. Mention may be made of titanium oxide, zirconium oxide or cerium oxide, and also zinc oxide, iron oxide or chromium oxide, ferric blue, chromium hydrate, carbon black, ultramarines (aluminosilicate polysulfides), manganese pyrophosphate and certain metallic powders such as silver or aluminum powder. Mention may also be made of the D&C pigments and lakes commonly used to give the lips and the skin a makeup effect, which are calcium, barium, aluminum, strontium or zirconium salts.

The nacres may be present in the composition in a proportion of from 0.01% to 20% by weight and preferably in a proportion of about from 3% to 10% by weight. Among the nacres that may be envisioned, mention may be made of natural mother-of-pearl, mica coated with titanium oxide, with iron oxide, with natural pigment or with bismuth oxychloride, and also colored titanium mica.

Among the liposoluble or water-soluble dyes that may be present in the composition, alone or as a mixture, in a proportion of from 0.001% to 15% by weight, preferably 0.01% to 5% by weight and especially from 0.1% to 2% by weight, relative to the total weight of the composition, mention may be made of the disodium salt of ponceau, the disodium salt of alizarin green, quinoline yellow, the trisodium salt of amaranth, the disodium salt of tartrazine, the monosodium salt of rhodamine, the disodium salt of fuchsin, xanthophyll, methylene blue, cochineal carmine, halo-acid dyes, azo dyes, anthraquinone dyes, copper sulfate, iron sulfate, Sudan brown, Sudan red and annatto, and also beetroot juice and carotene.

The composition according to the invention may also comprise one or more fillers, especially in a content ranging from 0.01% to 50% by weight and preferably ranging from 0.02% to 30% by weight, relative to the total weight of the composition. The fillers may be mineral or organic in any form, platelet-shaped, spherical or oblong. Mention may be made of talc, mica, silica, kaolin, polyamide (Nylon®) powder, poly-β-alanine powder and polyethylene powder, powders of tetrafluoroethylene polymers (Teflon®), lauroyllysine, starch, boron nitride, hollow polymer microspheres such as those of polyvinylidene chloride/acrylonitrile, for instance Expancel® (Nobel Industrie), of acrylic acid copolymers (Polytrap® from the company Dow Corning) and silicone resin microbeads (for example Tospearls® from Toshiba), elastomeric polyorganosiloxane particles, precipitated calcium carbonate, magnesium carbonate, magnesium hydrocarbonate, hydroxyapatite, hollow silica microspheres (Silica Beads® from Maprecos), glass or ceramic microcapsules, and metal soaps derived from organic carboxylic acids containing from 8 to 22 carbon atoms and preferably from 12 to 18 carbon atoms, for example zinc, magnesium or lithium stearate, zinc laurate or magnesium myristate.

The composition may also comprise an additional polymer such as a film-forming polymer. According to the present invention, the term "film-forming polymer" means a polymer capable, by itself or in the presence of an auxiliary film-forming agent, of forming a continuous film that adheres to a support and especially to keratin materials. Among the film-forming polymers that may be used in the composition of the present invention, mention may be made of synthetic polymers, of free-radical type or of polycondensate type, polymers of natural origin and mixtures thereof, in particular acrylic polymers, polyurethanes, polyesters, polyamides, polyureas and cellulose-based polymers, for instance nitrocellulose.

The composition may also advantageously comprise at least one surfactant that is generally present in an amount of between approximately 0.01% and 50% by weight, preferably between 0.1% and 40%, and even more preferably between 0.5% and 30% relative to the total weight of the composition.

This surfactant may be chosen from anionic, amphoteric, nonionic and cationic surfactants, or mixtures thereof.

The surfactants that are suitable for carrying out the present invention are especially, alone or as a mixture:

anionic surfactants, among which mention may be made, alone or as mixtures, of salts (in particular alkaline salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates and N-acyltaurates, the alkyl or acyl radical of all of these various compounds preferably containing from 8 to 24 carbon atoms, and the aryl radical preferably denoting a phenyl or benzyl group.

Mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms; alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, in particular those containing from 2 to 50 ethylene oxide groups, and mixtures thereof.

nonionic surfactants, among which mention may be made, alone or as mixtures, of polyethoxylated, polypropoxylated or polyglycerolated fatty acids, alkylphenols, α-diols or alcohols having a fatty chain containing, for example, 8 to 18 carbon atoms, it being possible for the number of ethylene oxide or propylene oxide groups to range in particular from 2 to 50 and for the number of glycerol groups to range in particular from 2 to 30.

Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides;

amphoteric surfactants, among which mention may be made, alone or as mixtures, of aliphatic secondary or tertiary amine derivatives in which the aliphatic radical is a linear or branched chain containing 8 to 22 carbon atoms and containing at least one water-soluble anionic group (for example carboxylate, sulfonate, sulfate, phosphate or phosphonate); mention may also be made of ($C_8$-$C_{20}$)alkylbetaines, sulfobetaines, ($C_8$-$C_{20}$)alkylamido($C_1$-$C_6$)alkylbetaines or ($C_8$-$C_{20}$)alkylamido($C_1$-$C_6$)alkylsulfobetaines;

cationic surfactants, among which mention may be made, alone or as mixtures, of:

A) the quaternary ammonium salts of general formula (XVI) below:

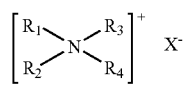

(XVI)

in which $X^-$ is an anion chosen from the group of halides (chloride, bromide or iodide) or ($C_2$-$C_6$)alkyl sulfates, more particularly methyl sulfate, phosphates, alkyl or alkylaryl sulfonates, anions derived from organic acid, such as acetate or lactate, and a) the radicals $R_1$ to $R_3$, which may be identical or different, represent a linear or branched aliphatic radical containing from 1 to 4 carbon atoms, or an aromatic radical such as aryl or alkylaryl. The aliphatic radicals can comprise heteroatoms such as, in particular, oxygen, nitrogen, sulfur or halogens. The aliphatic radicals are chosen, for example, from alkyl, alkoxy and alkylamide radicals, $R_4$ denotes a linear or branched alkyl radical containing from 16 to 30 carbon atoms.

The cationic surfactant is preferably a behenyltrimethylammonium salt (for example chloride).

b) the radicals $R_1$ and $R_2$, which may be identical or different, represent a linear or branched aliphatic radical containing from 1 to 4 carbon atoms, or an aromatic radical such as aryl or alkylaryl. The aliphatic radicals can comprise heteroatoms such as, in particular, oxygen, nitrogen, sulfur or halogens. The aliphatic radicals are chosen, for example, from alkyl, alkoxy, alkylamide and hydroxyalkyl radicals containing from about 1 to 4 carbon atoms;

$R_3$ and $R_4$, which may be identical or different, denote a linear or branched alkyl radical containing from 12 to 30 carbon atoms, said radical comprising at least one ester or amide function.

$R_3$ and $R_4$ are chosen in particular from ($C_{12}$-$C_{22}$)alkylamido($C_2$-$C_6$)alkyl and ($C_{12}$-$C_{22}$)alkylacetate radicals;

The cationic surfactant is preferably a stearamidopropyldimethyl(myristyl acetate) ammonium salt (for example chloride).

B)—the quaternary ammonium salts of imidazolinium, such as, for example, that of formula (XVII) below:

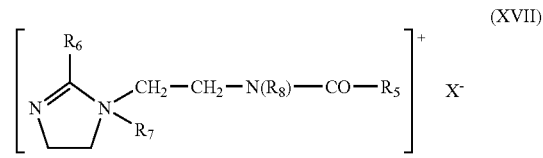

(XVII)

in which $R_5$ represents an alkenyl or alkyl radical containing from 8 to 30 carbon atoms, for example fatty acid derivatives of tallow, $R_6$ represents a hydrogen atom, a $C_1$-$C_4$ alkyl radical or an alkenyl or alkyl radical containing from 8 to 30 carbon atoms, $R_7$ represents a $C_1$-$C_4$ alkyl radical, $R_8$ represents a hydrogen atom or a $C_1$-$C_4$ alkyl radical, and X is an anion chosen from the group of halides, phosphates, acetates, lactates, alkyl sulfates, alkyl sulfonates or alkylaryl sulfonates. $R_5$ and $R_6$ preferably denote a mixture of alkenyl or alkyl radicals containing from 12 to 21 carbon atoms, such as, for example, fatty acid derivatives of tallow, $R_7$ denotes methyl and $R_8$ denotes hydrogen. Such a product is, for example, Quaternium-27 (CTFA 1997) or Quaternium-83 (CTFA 1997), which are sold under the names "Rewoquat" W75, W90, W75PG and W75HPG by the company Witco, C)—the diquaternary ammonium salts of formula (XVIII):

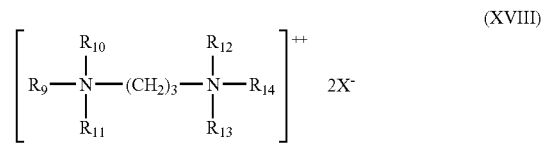

(XVIII)

in which $R_9$ denotes an aliphatic radical containing from about 16 to 30 carbon atoms, $R_{10}$, $R_{11}$, $R_{12}$, $R_{13}$ and $R_{14}$, which may be identical or different, are chosen from hydrogen and an alkyl radical containing from 1 to 4 carbon atoms, and X is an anion chosen from the group of halides, acetates, phosphates, nitrates and methyl sulfates. Such diquaternary ammonium salts in particular comprise propanetallowdiammmonium dichloride;

D)—the quaternary ammonium salts containing at least one ester function, of formula (XIX) below:

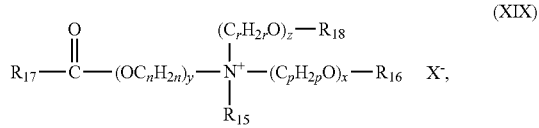

in which:

$R_{15}$ is chosen from $C_1$-$C_6$ alkyl radicals and $C_1$-$C_6$ hydroxyalkyl or dihydroxyalkyl radicals;

$R_{16}$ is chosen from:

a radical

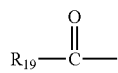

linear or branched, saturated or unsaturated $C_1$-$C_{22}$ hydrocarbon-based radicals $R_{20}$, a hydrogen atom, $R_{18}$ is chosen from:

a radical

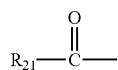

linear or branched, saturated or unsaturated $C_1$-$C_6$ hydrocarbon-based radicals $R_{22}$, a hydrogen atom, $R_{17}$, $R_{19}$ and $R_{21}$, which may be identical or different, are chosen from linear or branched, saturated or unsaturated $C_7$-$C_{22}$ hydrocarbon-based radicals;

n, p and r, which may be identical or different, are integers ranging from 2 to 6;

y is an integer ranging from 1 to 10;

x and z, which may be identical or different, are integers ranging from 0 to 10;

$X^-$ is a simple or complex, organic or inorganic anion; with the proviso that the sum x+y+z is from 1 to 15, that when x is 0, then $R_{16}$ denotes $R_{20}$ and that when z is 0, then $R_{18}$ denotes $R_{22}$.

The composition according to the invention may also comprise ingredients commonly used in cosmetics, such as vitamins, fragrances, nacres, thickeners, gelling agents, trace elements, softeners, sequestrants, fragrances, acidifying or basifying agents, preserving agents, sunscreens, surfactants, antioxidants, hair-loss counteractants, antidandruff agents, propellants and ceramides, or mixtures thereof. Needless to say, a person skilled in the art will take care to select this or these optional additional compound(s), and/or the amount thereof, such that the advantageous properties of the composition according to the invention are not, or are not substantially, adversely affected by the envisioned addition.

The composition according to the invention may be in the form of a suspension, a dispersion, especially of oil in water by means of vesicles; an optionally thickened or even gelled oily solution; an oil-in-water, water-in-oil or multiple emulsion; a gel or a mousse; an oily or emulsified gel; a dispersion of vesicles, especially lipid vesicles; a two-phase or multiphase lotion; a spray. This composition may have the appearance of a lotion, a cream, a pomade, a soft paste, an ointment, a solid cast or molded especially in stick or dish form, or alternatively a compacted solid.

A person skilled in the art may select the appropriate galenical form, and also the method for preparing it, on the basis of his general knowledge, taking into account, firstly, the nature of the constituents used, especially their solubility in the support, and, secondly, the intended use of the composition.

The cosmetic composition according to the invention may be in the form of a care and/or makeup product for bodily or facial skin, the lips and the hair, an antisun or self-tanning product, or even a haircare product.

It especially finds a particularly advantageous use in the field of haircare, especially for holding the hairstyle or shaping the hair. The hair compositions are preferably shampoos, hairsetting gels or lotions, blow-drying lotions, and fixing and styling compositions such as lacquers or sprays. The lotions may be packaged in various forms, especially in vaporizers or pump-dispenser bottles or in aerosol containers in order to apply the composition in vaporized form or in the form of a mousse.

In one preferred embodiment, the compositions in accordance with the invention may be used for washing or treating keratin materials such as the hair, the skin, the eyelashes, the eyebrows, the nails, the lips and the scalp, and more particularly the hair.

The compositions according to the invention may be detergent compositions such as shampoos, shower gels and bubble baths. In this embodiment of the invention, the compositions comprise at least one washing base, which is generally aqueous.

A subject of the invention is thus also a process for treating keratin materials such as the skin or the hair, characterized in that it consists in applying to the keratin materials a cosmetic composition as defined above, and then optionally in rinsing with water.

Thus, this process according to the invention allows hold of the hairstyle, and treatment, washing or care of or makeup-removal from the skin, the hair or any other keratin material.

In another preferred embodiment, the compositions of the invention may be in the form of a rinse-out or leave-in hair conditioner, compositions for permanent-waving, relaxing, dyeing or bleaching the hair, or alternatively in the form of rinse-out compositions, to be applied before or after dyeing, bleaching, permanent-waving or relaxing the hair, or alternatively between the two steps of a permanent-waving or hair-relaxing operation.

When the composition is in the form of a hair conditioner optionally to be rinsed out, it advantageously contains at least one cationic surfactant, for example in a concentration generally of between 0.1% and 10% by weight and preferably from 0.5% to 5% by weight relative to the total weight of the composition.

The compositions of the invention may also be in the form of washing compositions for the skin, in particular in the form of bath or shower solutions or gels or makeup-removing products.

The compositions according to the invention may also be in the form of aqueous or aqueous-alcoholic lotions for skincare and/or haircare.

A subject of the invention is also a cosmetic process for making up or caring for keratin materials, especially bodily or facial skin, the nails, the hair and/or the eyelashes, comprising the application to said materials of a cosmetic composition as defined above.

The invention is illustrated in greater detail in the examples that follow.

Measurement of the Tg

A film is made using an aqueous solution containing 6% by weight of polymer and dried for 48 hours under a controlled atmosphere at 50% relative humidity and 25° C. The films thus obtained have a thickness of between 10 and 20 μm.

The measuring apparatus is a DSC (TA Instruments).

The sample obtained from the film is placed in a hermetic crucible and is heated according to the following protocol:

equilibrium at initial temperature Ti;

heating 1: raising of the temperature, at a rate of +10° C./min to a final temperature: Tf (° C.);

isotherm for 1 minute;

reducing of the temperature at a rate of −10° C./min to Ti (° C.);

heating 2: raising of the temperature at a rate of +10° C./min to Tf (° C.);

isotherm for 1 minute, with Ti: initial temperature −120° C.

with Tf: final temperature +120° C.

The Tg values are measured during the heating steps 1 and 2.

Measurement of the Water Uptake

About 1 g of dry polymer is placed in an aluminum crucible 4.5 cm in diameter (0.01 m$^2$). It is left to dry for 48 hours in an oven at 60° C. under reduced pressure. The crucibles are removed and weighed immediately (less than one minute after removing from the oven). W1 is obtained.

The crucibles are then placed in a glove box with a given relative humidity (75% RH or 85% RH) and are left therein for 6 hours. They are then weighed again immediately after removing them from the glove box. W2 is obtained.

The water uptake is calculated in the following manner:

$$[(W2-W1) \times 100]/W1$$

EXAMPLE 1

75 ml of methyl ethyl ketone (MEK) are placed in a reactor (4-necked flask) on which are mounted two addition funnels, a condenser and a mechanical stirrer, and are brought to 80° C.

In parallel, a solution 1 is prepared comprising the monomers: 50 g of polyethylene glycol methacrylate (MPEG 550), 50 g of dimethylaminopropylmethacrylamide (DMAPMA) and the initiator: 0.5 g of (Trigonox 21S).

A solution 2 is also prepared, comprising 75 ml of methyl ethyl ketone and 0.5 g of initiator (Trigonox 21S).

Solution 1 is poured dropwise over 1 hour and solution 2 over two hours, into the 4-necked flask reactor. The resulting mixture is then maintained at 80° C. for 5 hours. The orange-yellow solution obtained is cooled. 95 g of polymer are obtained.

The polymer has a Brookfield viscosity at 15% in MEK, at 25° C., measured with a No. 1 needle-type spindle, at a speed of 0.1 rpm, of 7.5 mPa·s.

The polymer may then be neutralized in the following manner: 290 ml of 1N HCl are added with stirring to the 95 g of polymer and 200 ml of distilled water. The solvent (MEK) is then evaporated off.

The neutralized polymer is soluble in water (at least up to 50% by weight).

Its Tg is −60° C.

The neutralized polymer has a water uptake at 85% RH of 51%.

EXAMPLE 2

100 ml of water are placed in a reactor (4-necked flask) on which are mounted two addition funnels, a condenser and a mechanical stirrer, and are brought to 80° C.

In parallel, a solution 1 comprising 50 g of monomer MPEG 550, 1 g of initiator (potassium persulfate KPS) and 50 ml of water is prepared.

A solution 2 comprising 50 g of monomer DMAPMA 100% neutralized with betaine hydrochloride, and 50 g of water, is also prepared.

Solutions 1 and 2 are poured into the 4-necked flask over 1 hour. After 1 hour at 80° C., a mixture of 1 g of KPS in 50 ml of water is added dropwise thereto over 15 minutes.

The resulting mixture is then maintained at 80° C. for 3 hours. 90 g of polymer neutralized with betaine hydrochloride are obtained.

The polymer has a Brookfield viscosity at 15% in water, at 25° C., measured with a No. 1 needle-type spindle, at a speed of 6 rpm, of 164 mPa·s.

The polymer is soluble in water (at least up to 50% by weight).

Its Tg is −60° C.

The neutralized polymer has a water uptake at 85% HR of 90%.

PREPARATION EXAMPLES 3 TO 14

The following polymers according to the invention are prepared according to the process of Example 1 (solvent process) or of Example 2 (process in water):

| Example | Monomers (weight %) | | Process and neutralization | Solubility |
|---|---|---|---|---|
| Example 3 | MPEG 550 | 10% | Process 1 | water |
| | DMAPMA | 90% | HCl | |
| Example 4 | MPEG 1100 | 25% | Process 1 | water |
| | DMAPMA | 75% | HCl | |
| Example 5 | MPEG 1100 | 50% | Process 1 | water |
| | DMAPMA | 50% | HCl | |
| Example 6 | MPEG 550 | 50% | Process 1 | water |
| | DMAPMA | 50% | HCl | |
| Example 7 | MPEG 550 | 50% | Process 2 | water |
| | SPE | 50% | no neutralization | |
| Example 8 | MPEG 550 | 50% | Process 1 | water |
| | DMAEMA | 50% | HCl | |
| Example 9 | MPEG 550 | 50% | Process 1 | water |
| | Morpholinoethyl methacrylate | 50% | HCl | |
| Example 10 | MPEG 2000 | 50% | Process 2 | water |
| | DMAPMA | 50% | no neutralization | |
| Example 11 | MPEG 550 | 50% | Process 1 | water |
| | DMAPMA | 50% | betaine hydrochloride | |
| Example 12 | MPEG 550 | 40% | Process 1 | water |
| | DMAPMA | 35% | HCl | |
| | Acrylic acid | 15% | | |

| Example | Monomers (weight %) | | Process and neutralization | Solubility |
|---|---|---|---|---|
| Example 13 | MPEG 550 DMAPMA | 50% 50% | Process 1 20% behenic acid | water-dispersible |
| Example 14 | MPEG 550 DMAPMA | 50% 50% | Process 1 oleic acid | water-dispersible |

MPEG: polyethylene glycol methacrylate (with MW = 550, 1100 or 2000)
DMAPMA: dimethylaminopropylmethacrylamide
SPE: N,N-dimethyl-N-(2-methacryloyloxyethyl)-N-(3-sulfopropyl)ammonium betaine
DMAEMA: dimethylaminoethyl methacrylate

EXAMPLE 15

A composition comprising the following constituents (weight %) is prepared:
  7.5% lauryl ether sulfate
  2.5% cocobetaine amphoteric surfactant
  5% cocopolyglucoside surfactant
  1.5% polymer of Example 11
  qs 100% water The shampoo composition obtained gives a good styling effect. The cosmetic nature on wet hair is satisfactory. The styling results obtained after application to heads are good and the cosmetic properties on dry hair are particularly good. It is found that this composition provides cosmetic properties equivalent to those provided by a common conditioning shampoo: cosmetic nature superior to that of the prior art for equivalent styling; certain cosmetic criteria (smoothing, softness and sheen) are better with the composition according to the invention.

EXAMPLE 16

A composition comprising the following constituents (weight %) is prepared:
  7.5% lauryl ether sulfate
  2.5% cocobetaine amphoteric surfactant
  5% cocopolyglucoside surfactant
  1.5% polymer of Example 13
  qs 100% water The resulting composition is applied to heads in a single application, and the following criteria are evaluated (panel of six individuals):
  on wet hair: the smoothing and disentangling
  on dry hair: the bounce of the rolled-up and dried lock (styling effect), disentangling and sheen.

The following results are obtained:
  on wet hair, the disentangling and sheen are very good;
  on dry hair, the styling effect is good; the cosmetic properties are good, superior to those of the prior art for an equivalent styling effect; certain cosmetic criteria (smoothing, softness and sheen) are better with the composition according to the invention.

The results are collated in the table below:

| | Disentangling wet hair | Smoothing wet hair | Disentangling dry hair | Sheen | Bounce |
|---|---|---|---|---|---|
| Composition of Ex. 15 | +++ | +++ | +++ | +++ | ++ |
| Composition of Ex. 16 | ++++ | ++++ | | ++++ | ++++ |
| Control (DOP camomile shampoo) | ++ | ++ | ++ | ++ | 0 |

EXAMPLE 17

Comparative Examples

In a first stage, the polymers below, not in accordance with the invention, are prepared according to Example 1:

| | | | |
|---|---|---|---|
| Comparative 1 (additional hydrophobic monomer) | MPEG 550 DMAPMA Ethylhexyl acrylate | 35% 50% 15% 15% | Process 1 HCl |
| Comparative 2 (additional hydrophobic monomer) | MPEG 550 DMAPMA Ethylhexyl acrylate | 50% 15% 35% | Process 1 HCl |
| Comparative 3 (crosslinked polymer) | MPEG 550 DMAPMA Butanediol dimethacrylate | 50% 50% 1% | Process 1 HCl |
| Comparative 4 | MPEG 550 DMAPMA | 94% 6% | Process 1 HCl |
| Comparative 5 | MPEG 550 DMAPMA | 6% 94% | Process 1 neutralized HCl |
| Comparative 6 | MPEG 550 TMEACL* | 50% 50% | |
| Comparative 7 (absence of MPEG) | Ethyl vinyl ether DMAPMA | 50% 50% | Process 1 neutralized HCl |
| Comparative 8 | MPEG 550 DMAPMA EEMA | 40% 50% 10% | Process 1 neutralized HCl |

*TMEACL: 2-(dimethylamino)ethyl acrylate, quaternized with methyl chloride
*EEMA: ethoxyethyl methacrylate A composition comprising the following constituents is prepared (weight %):
  7.5% lauryl ether sulfate
  2.5% cocobetaine amphoteric surfactant (Dehyton AB30 from Cognis)
  5% cocopolyglucoside surfactant (Plantacare 818 UP from Cognis)
  3% polymer (or polymer mixture)
  qs 100% water The resulting composition is applied to heads in a single application, and the following criteria are evaluated (panel of 6 individuals):
  on wet hair: the smoothing and the disentangling
  on dry hair: the bounce of the rolled-up and dried lock (styling effect)

These compositions not in accordance with the invention are compared with a composition in accordance with the invention comprising the polymer of Example 11 (composition C1).

The results are collated in the following tables:

| Polymer contained in the composition | Observations |
|---|---|
| Comparative polymer 4 | on wet hair: disentangling and smoothing inferior to those of composition C1<br>on dry hair: bounce inferior to that of composition C1<br>non-styling |
| Comparative polymer 5 | on wet hair: disentangling and smoothing inferior to those of composition C1<br>on dry hair: bounce inferior to that of composition C1<br>non-styling |
| Comparative polymer 6 | on wet hair: disentangling and smoothing inferior to those of composition C1; lock less slippery than with C1<br>on dry hair: bounce less than that of composition C1; curl more relaxed and less tonic than with C1; more rustly feel than with C1 |
| Comparative polymer 7 | on wet hair: disentangling and smoothing inferior to those of composition C1; lock more rustly than with C1<br>on dry hair: bounce inferior to that of composition C1; curl more relaxed, less tonic than with C1 |
| Comparative polymer 8 | on wet hair: disentangling and smoothing inferior to those of composition C1<br>on dry hair: bounce similar to that of composition C1 |

| Polymer present in the composition | Disentangling of wet hair | Feel | Bounce | Styling |
|---|---|---|---|---|
| Example 11 | +++ | + | ++ | ++ |
| 50/50 DMAPMA/poly-ethylene glycol mixture | +++ | lathering problem | + | 0 |
| Comparative polymer 1 | ++ | − | + | 0 |
| Comparative polymer 2 | ++ | − | +++ | 0 |
| Comparative polymer 3 | + | − | +++ | 0 |

EXAMPLE 18

A composition comprising the following constituents (weight %) is prepared:
6% polymer of Example 1
0.001% preserving agent
qs 100% water The composition is introduced into a pump-dispenser bottle; it is applied to dry and styled hair, and the following criteria are evaluated: the bounce of the rolled-up and dried lock (styling effect). It is found that the styling effect is very good: the treated lock is very manageable; the hair has more volume compared with the prior art.

EXAMPLE 19

A shampoo comprising the following constituents (weight %) is prepared:
7.5% lauryl ether sulfate
2.5% cocobetaine amphoteric surfactant (Dehyton AD30 from Cognis)
5% cocopolyglucoside surfactant (Plantacare 818 UP from Cognis)
qs preserving agent
1.5% polymer active material
qs 100% water The resulting composition is applied to heads in a single application, and the following criteria are evaluated (panel of four individuals):
on wet hair: the smoothing, lightness and ease of disentangling
on dry hair: the bounce of the rolled-up and dried lock (styling effect).

The following results are obtained:

| Polymer | MPEG 550/DMAPMA 50/50 neutralized with betaine hydrochloride |
|---|---|

On wet hair: the composition provides smoothness, ease of disentangling and lightness;
On dried hair: the composition gives mass, suppleness, volume and smoothing to the hair.

The invention claimed is:

1. An ethylenic copolymer, which is not cross-linked, consisting essentially of, as a weight percentage relative to the total weight of the copolymer:
a) an amount ranging from 10% to 60% by weight of at least one monomer chosen from monomers of formula (I) and salts thereof:

$$H_2C=C\begin{subarray}{l}R_1\\ (Z)_x-(R_2)_m-(CH_2CH_2O)_n-R_3\end{subarray} \quad (I)$$

wherein:
$R_1$ is chosen from hydrogen, linear hydrocarbon-based radicals of the type $C_pH_{2p+}$, wherein p ranges from 1 to 12, and branched hydrocarbon-based radicals of the type $C_pH_{2p+1}$, wherein p ranges from 1 to 12;
Z is a divalent group chosen from —COO—, —CONH—, —CONCH$_3$—, —OCO—, —O—, —SO$_2$—, —CO—O—CO—, and —CO—CH$_2$—CO—;
x is 0 or 1;
$R_2$ is chosen from a saturated or unsaturated, optionally aromatic, linear, branched, or cyclic carbon-based divalent radicals of 1 to 30 carbon atoms, optionally comprising 1 to 18 heteroatoms chosen from O, N, S, F, Si, and P;
m is 0 or 1;
n ranges from 3 to 300;
$R_3$ is chosen from hydrogen and saturated or unsaturated, optionally aromatic, linear, branched, or cyclic carbon-based radicals of 1 to 30 carbon atoms, optionally comprising 1 to 20 heteroatoms chosen from O, N, S, F, Si, and P;
the at least one monomer of formula (I) has a molecular weight ranging from 500 to 13,000 g/mol; and
b) an amount ranging from 40% to 90% by weight of at least one essentially cationic monomer chosen from:
(i) cationic monomers of formula (IIa) and salts thereof,
(ii) amphoteric monomers of formula (IIc), salts thereof, amphoteric monomers of formula (IId), and salts thereof, and (iii) a mixture of (1) at least one cationic monomer chosen from cationic monomers of formula (IIa) and salts thereof and (2) at least one at least one monomer chosen from (a) anionic monomers chosen from maleic anhydride, monomers of formula (IIb), and salts thereof, and
(b) amphoteric monomers chosen from monomers of formulae (IIc) and salts thereof, amphoteric monomers chosen from monomers of formulae (IId), and salts thereof;

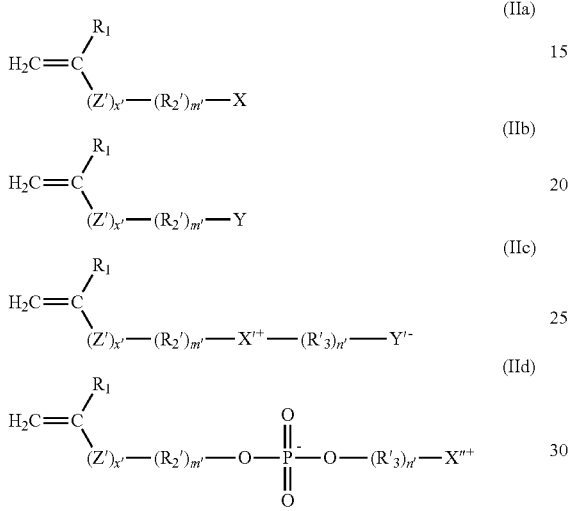

wherein:
$R_1$ is chosen from hydrogen; linear hydrocarbon-based radicals of the type $C_pH_{2p+1}$, wherein p ranges from 1 to 12; and branched hydrocarbon-based radicals of the type $C_pH_{2p+1}$, wherein p ranges from 1 to 12;
Z' is a divalent group chosen from —COO—, —CONH—, —CONCH$_3$—, —OCO—, —O—, —SO$_2$—, —CO—O—CO—, and —CO—CH$_2$—CO—;
x' is 0 or 1;
$R_2'$ is chosen from a saturated or unsaturated, optionally aromatic, linear, branched, or cyclic divalent carbon-based radical of 1 to 30 carbon atoms, optionally comprising 1 to 18 heteroatoms chosen from O, N, S, F, Si, and P;
m' is 0 or 1;
X, in formula (IIa), is chosen from:
(a) guanidino groups and amidino groups;
(b) groups of formula —N($R_6$)($R_7$), groups of formula —P($R_6$)($R_7$), and groups of formula —P$^+R_6R_7R_8$, wherein
$R_6$, $R_7$, and $R_8$, which may be identical or different, are chosen from
(i) hydrogen,
(ii) linear, branched, or cyclic, saturated or unsaturated, optionally aromatic alkyl groups comprising from 1 to 18 carbon atoms, and optionally comprising 1 to 10 heteroatoms chosen from O, N, S, F, Si, and P; and
(iii) $R_6$ and $R_7$ form together with the nitrogen or phosphorus atom to which they are attached a saturated or unsaturated, optionally aromatic ring comprising 5 to 8 atoms, wherein said ring may optionally be fused with at least one other saturated or unsaturated, optionally aromatic ring comprising 5 to 7 atoms; and
(c) —R'$_6$—N—R'$_7$— groups, wherein R'$_6$ and R'$_7$ form together with the nitrogen atom a saturated or unsaturated, optionally aromatic ring comprising 5 to 8 atoms; said ring may optionally be fused with at least one other saturated or unsaturated, optionally aromatic ring comprising 5 to 7 atoms;
Y is chosen from —COOH, —SO$_3$H, —OSO$_3$H, —PO$_3$H$_2$, and —OPO$_3$H$_2$;
$X'^+$ is a divalent group of formula —N$^+$(R$_6$)(R$_7$)—, wherein $R_6$ and $R_7$, which may be identical or different, are chosen from (i) hydrogen, (ii) linear, branched, or cyclic, optionally aromatic alkyl groups comprising from 1 to 25 carbon atoms, optionally comprising 1 to 20 heteroatoms chosen from O, N, S, and P; and (iii) $R_6$ and $R_7$ form together with the nitrogen atom a saturated or unsaturated, optionally aromatic ring comprising 5 to 8 atoms, said ring optionally fused with at least one other saturated or unsaturated, optionally aromatic ring comprising 5 to 8 atoms;
Y'$^-$ is a group chosen from —COO$^-$, —SO$_3^-$, —OSO$_3^-$, —PO$_3^{2-}$, and —OPO$_3^{2-}$;
R'$_3$ is chosen from saturated or unsaturated, optionally aromatic, linear, branched, or cyclic divalent carbon-based radicals of 1 to 30 carbon atoms, optionally comprising 1 to 18 heteroatoms chosen from O, N, S, F, Si, and P;
n' ranges from 1 to 100;
X''$^+$ is chosen from groups of formula —N$^+R_6R_7R_8$, wherein $R_6$, $R_7$, and $R_8$, which may be identical or different, are chosen from (i) hydrogen, (ii) linear, branched, or cyclic, optionally aromatic alkyl groups comprising 1 to 18 carbon atoms, optionally comprising 1 to 5 heteroatoms chosen from O, N, S, and P; and (iii) $R_6$ and $R_7$ form together with the nitrogen atom a first saturated or unsaturated, optionally aromatic ring comprising 5 to 7 atoms, said ring optionally fused with at least one other saturated or unsaturated, optionally aromatic ring comprising 5 to 7 atoms;
and salts of said ethylenic copolymer.

2. The copolymer according to claim 1, wherein, in formula (I), $R_1$ is chosen from hydrogen, methyl, ethyl, propyl, and butyl.

3. The copolymer according to claim 1, wherein, in formula (I), Z is chosen from —COO and —CONH.

4. The copolymer according to claim 1, wherein, in formula (IIa), formula (IIb), formula (IIc), and formula (IId), $R_1$ is chosen from hydrogen, methyl, ethyl, propyl, and butyl.

5. The copolymer according to claim 1, wherein, in formula (I), the radical $R_2$ is chosen from:
alkylene radicals;
phenylene radicals —C$_6$H$_4$—, optionally substituted at the ortho-, meta-, or para-position with a $C_1$-$C_{12}$ alkyl radical optionally comprising 1 to 25 heteroatoms chosen from O, N, S, F, Si, and P;

benzylene radicals —C₆H₄—CH₂—, optionally substituted with a C₁-C₁₂ alkyl radical optionally comprising 1 to 8 heteroatoms chosen from O, N, S, F, Si, and P;

pyridinium radicals of formula:

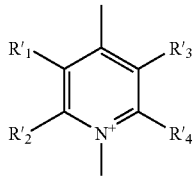

wherein R'₁ to R'₄, which may be identical or different, are chosen from hydrogen and C₁-C₁₂ alkyl radicals optionally comprising 1 to 8 heteroatoms chosen from O, N, S, F, Si, and P; and —CH₂—CHOH—, —CH₂—CH₂—CHOH—, CH₂—CH₂—CH(NH₂)—, —CH₂—CH(NH₂)—, —CH₂—CH₂—CH(NHR')—, —CH₂—CH(NHR')—, —CH₂—CH₂—CH(NR'R")—, —CH₂—CH(NR'R")—, —CH₂—CH₂—CH₂—NR'—, —CH₂—O—CO—O—, CH₂—CH₂—O—CO—O—, —CH₂—CO—O—, —CH₂—CH₂—CO—O—, —CH₂—O—CO—NH—, —CH₂—CH₂—O—CO—NH—, —CH₂—NH—CO—NH—, —CH₂—CH₂—NH—CO—NH—, —CH₂—CH₂—CH₂—O—, and —CH₂—CH₂—CHR'—O—, wherein R' and R", which may be identical or different, are chosen from linear or branched C₁-C₂₂ alkyl radicals optionally comprising 1 to 12 heteroatoms chosen from O, N, S, F, Si, and P.

6. The copolymer according to claim 4, wherein, in formula (I), R₂ is chosen from methylene, ethylene, propylene, n-butylene, isobutylene, tert-butylene, n-hexylene, n-octylene, n-dodecylene, n-octadecylene, n-tetradecylene, and n-docosanylene.

7. The copolymer according to claim 5, wherein R'₁ to R'₄ are chosen, independently of one another, from methyl and ethyl.

8. The copolymer according to claim 1, wherein, in formula (I), n ranges from 5 to 200.

9. The copolymer according to claim 1, wherein, in formula (I), R₃ is chosen from hydrogen, succinimido radicals, maleimido radicals, mesityl radicals, tosyl radicals, triethoxysilane radicals, phthalimide radicals, —CH₂—CH₂CN radicals, benzyl radicals optionally substituted with a C₁-C₁₂ alkyl radical optionally comprising 1 to 8 heteroatoms chosen from O, N, S, F, Si, and P, phenyl radicals optionally substituted with a C₁-C₁₂ alkyl radical optionally comprising 1 to 8 heteroatoms chosen from O, N, S, F, Si, and P, C₁-C₃₀ alkyl radicals optionally comprising 1 to 18 heteroatoms chosen from O, N, S, F, Si, and P;

wherein said benzyl, phenyl, and alkyl radicals optionally comprise a function chosen from succinimido, glutarate-succinimido, glutarate, maleimido, mesityl, benzoate, tosyl, triethoxysilane, phthalimide, thioester, benzotriazole carbonate, butyraldehyde, acetaldehyde diethyl acetal, biotin, phospholipid, succinate, N-hydroxysuccinimide, —SO₃H, —COOH, —PO₄, —NR₅R₆, and —N⁺R₅R₆R₇, wherein R₅, R₆, and R₇, which may be identical or different, are chosen from hydrogen and linear, branched, or cyclic C₁-C₁₈ alkyl radicals, optionally comprising at least one heteroatom and optionally comprising at least one protecting group.

10. The copolymer according to claim 1, wherein said at least one monomer of formula (I) is chosen from:
poly(ethylene glycol) (meth)acrylate;
methylpoly(ethylene glycol) (meth)acrylate;
alkylpoly(ethylene glycol) (meth)acrylates;
phenylpoly(ethylene glycol) (meth)acrylates; and
monomers of the following formula:

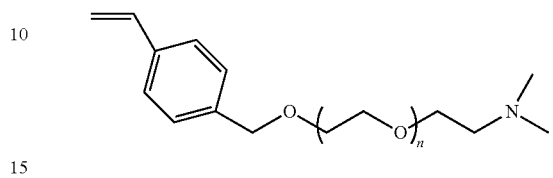

wherein n ranges from 3 to 100.

11. The copolymer according to claim 1, wherein the at least one monomer of formula (I) is present in an amount ranging from 20% to 55% by weight, relative to the total weight of the polymer.

12. The copolymer according to claim 1, wherein, in formulae (IIa), (IIb), (IIc), and (IId), R'₂ is chosen from:
alkylene radicals;
phenylene radicals —C₆H₄—, optionally substituted at the ortho-, meta-, or para-position with a C₁-C₁₂ alkyl radical optionally comprising 1 to 5 heteroatoms chosen from N, O, S, F, Si, and, P; and
benzylene radicals —C₆H₄—CH₂—, optionally substituted with a C₁-C₁₂ alkyl radical optionally comprising 1 to 5 heteroatoms chosen from O, N, S, F, Si, and P;
a radical of formula —CH₂—O—CO—O—, CH₂—CH₂—O—CO—O—, —CH₂—CO—O—, —CH₂—CH₂—CO—O—, —[(CH₂)₅—CO—O]ₙ—, —CH₂—CH(CH₃)—O—, —(CH₂)₂—O—, —CH₂—O—CO—NH—, —CH₂—CH₂—O—CO—NH—; —CH₂—NH—CO—NH—, —CH₂—CH₂—NH—CO—NH—, —CH₂—CHOH—, —CH₂—CH₂—CHOH—, —CH₂—CH₂—CH(NH₂)—, —CH₂—CH(NH₂)—, —CH₂—CH₂—CH(NHR')—, —CH₂—CH(NHR')—, —CH₂—CH₂—CH(NR'R")—, —CH₂—CH(NR'R")—, —CH₂—CH₂—CH₂—NR'—, —CH₂—CH₂—CH₂—O—, and —CH₂—CH₂—CHR'—O—, wherein R' and R", which may be identical or different, are chosen from linear or branched C₁-C₂₂ alkyl radicals optionally comprising 1 to 12 heteroatoms chosen from O, N, S, F, Si, and P.

13. The copolymer according to claim 1, wherein, in formula (IIa), R₆ and R₇ in X are, independently of one another, chosen from hydrogen, methyl groups, ethyl groups, propyl groups, isopropyl groups, n-butyl groups, t-butyl groups, isobutyl groups, octyl groups, lauryl groups, and stearyl groups.

14. The copolymer according to claim 1, wherein the cationic monomers of formula (IIa) are chosen from dimethylaminopropyl(meth)acrylamide, dimethylaminoethyl(meth)acrylamide, diethylaminoethyl(meth)acrylate, dimethylaminoethyl(meth)acrylate, vinylimidazole, vinylpyridine, and morpholinoethyl(meth)acrylate, and the monomers below:

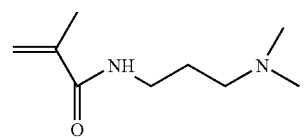

-continued

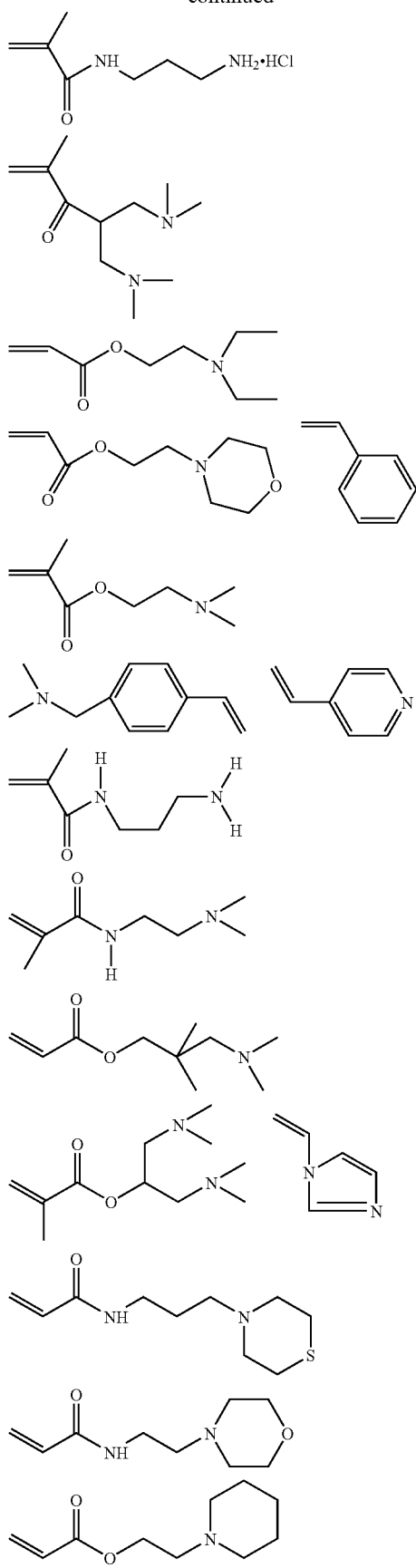
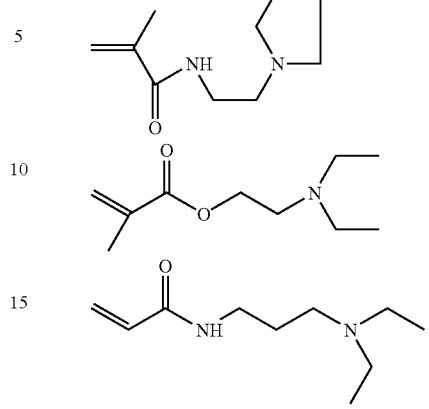

15. The copolymer according to claim 1, wherein the cationic monomers of formula (IIa) are chosen from dimethylaminopropyl(meth)acrylamide, dimethylaminoethyl(meth)acrylamide, diethylaminoethyl (meth)acrylate, dimethylaminoethyl(meth)acrylate, vinylimidazole, vinylpyridine, and morpholinoethyl(meth)acrylate.

16. The copolymer according to claim 1, wherein the anionic monomers are chosen from maleic anhydride, acrylic acid, methacrylic acid, crotonic acid, itaconic acid, fumaric acid, maleic acid, 2-carboxyethyl acrylate ($CH_2$=CH—C(O)—O—$(CH_2)_2$—COOH), styrenesulfonic acid, 2-acrylamido-2-methylpropanesulfonic acid, vinylbenzoic acid, vinylphosphoric acid, sulfopropyl(meth)acrylate, and salts thereof.

17. The copolymer according to claim 1, wherein at least one of monomers of formula (IIc) and monomers of formula (IId) are chosen from N,N-dimethyl-N-(2-methacryloyloxyethyl)-N-(3-sulfopropyl)ammonium betaine, N,N-dimethyl-N-(3-methacrylamidopropyl)-N-(3-sulfopropyl)ammonium betaine, 1-(3-sulfopropyl)-2-vinylpyridinium betaine, and 2-methacryloyloxyethylphosphorylcholine.

18. The copolymer according to claim 1, wherein the at least one essentially cationic monomer is present in an amount ranging from 45% to 80% by weight, relative to the total weight of the polymer.

19. The copolymer according to claim 1, wherein at least one of the monomers and the polymer is neutralized with at least one neutralizer chosen from mineral bases, organic bases, mineral acids, and organic acids.

20. The copolymer according to claim 1, wherein at least one of the monomers and the polymer is neutralized with at least one neutralizer chosen from mineral neutralizers and organic acid neutralizers with a log P value of less than or equal to 2.

21. The copolymer according to claim 1, wherein at least one of the monomers and the polymer is neutralized with at least one neutralizer chosen from 2-ethylcaproic acid, oleic acid, behenic acid, stearic acid, acetic acid, citric acid, tartaric acid, betaine hydrochloride, and gluconic acid.

22. The copolymer according to claim 1, wherein:
the at least one monomer of formula (I) is present in an amount ranging from 10% to 60% by weight, relative to the total weight of the polymer, and is chosen from poly(ethylene glycol) (meth)acrylates and methylpoly(ethylene glycol) (meth)acrylates; and/or
the at least one essentially cationic monomer is present in an amount ranging from 40% to 90% by weight, relative to the total weight of the polymer, and is chosen from the monomers of formula (IIb).

23. The copolymer according to claim 1, wherein:
the at least one monomer of formula (I) is present in an amount ranging from 10% to 60% by weight, relative to the total weight of the polymer, and is chosen from poly(ethylene glycol) (meth)acrylates; and
the at least one essentially cationic monomer is present in an amount ranging from 40% to 90% by weight, relative to the total weight of the polymer, and is chosen from dimethylaminopropyl(meth)acrylamide, dimethylaminoethyl(meth)acrylamide, diethylaminoethyl(meth)acrylate, dimethylaminoethyl(meth)acrylate, vinylimidazole, vinylpyridine, and morpholinoethyl(meth)acrylate.

24. The copolymer according to claim 1, wherein:
the at least one monomer of formula (I) is present in an amount ranging from 10% to 60% by weight, relative to the total weight of the polymer, and is chosen from poly(ethylene glycol) (meth)acrylates; and
the at least one essentially cationic monomer is present in an amount ranging from 40% to 90% by weight relative to the total weight of the polymer and is chosen from dimethylaminopropyl(meth)acrylamide, dimethylaminoethyl(meth)acrylamide, diethylaminoethyl(meth)acrylate, dimethylaminoethyl(meth)acrylate, vinylimidazole, vinylpyridine, and morpholinoethyl(meth)acrylate; and
the polymer is neutralized with at least one neutralizer chosen from 2-ethylcaproic acid, oleic acid, behenic acid, stearic acid, acetic acid, citric acid, tartaric acid, betaine hydrochloride, and gluconic acid.

25. The copolymer according to claim 1, wherein:
the at least one monomer of formula (I), alone or as a mixture, is present in an amount ranging from 10% to 60% by weight, relative to the total weight of the polymer, and is chosen, alone or as a mixture, from poly(ethylene glycol) (meth)acrylates; and
the at least one essentially cationic monomer is present in an amount ranging from 40% to 90% by weight relative to the total weight of the polymer and is chosen, alone or as a mixture, from dimethylaminopropyl(meth)acrylamide, and
the polymer is neutralized with at least one neutralizer chosen from behenic acid and betaine hydrochloride.

26. The copolymer according to claim 1, wherein said polymer is conveyable in aqueous medium.

27. The copolymer according to claim 26, wherein said aqueous medium is water-soluble or water-dispersible.

28. The copolymer according to claim 1, wherein said polymer has a viscosity in water ranging from 1 mP·s to 1000 mPa·s, measured at 25° C., using a Brookfield viscometer, for a solution containing 15% by weight of the polymer in water or methyl ethyl ketone, at 25° C., with a No. 1 spindle of needle type; for a measuring time of 5 minutes, at a speed ranging from 0.1 rpm to 6 rpm.

29. The copolymer according to claim 1, wherein said polymer has a glass transition temperature (Tg) ranging from −150° C. to 20° C.

30. The copolymer according to claim 1, wherein said polymer has a water uptake ranging from 3% to 150% by weight, at 75% relative humidity (75% RH); and said polymer has a water uptake ranging from 3% to 200% by weight, at 85% relative humidity (85% RH).

31. A cosmetic or pharmaceutical composition comprising, in a physiologically acceptable medium, at least one copolymer, which is not cross-linked, consisting essentially of, as a weight percentage relative to the total weight of the polymer:
a) an amount ranging from 10% to 60% by weight of at least one monomer chosen from monomers of formula (I) and salts thereof:

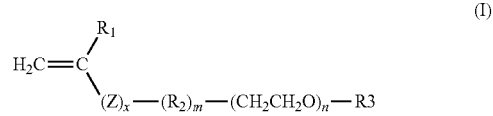

(I)

wherein:
$R_1$ is chosen from hydrogen, linear hydrocarbon-based radicals of the type $C_pH_{2p+1}$, wherein p ranges from 1 to 12, and branched hydrocarbon-based radicals of the type $C_pH_{2p+1}$, wherein p ranges from 1 to 12;
Z is a divalent group chosen from —COO—, —CONH—, —CONCH$_3$—, —OCO—, —O—, —SO$_2$—, —CO—O—CO—, and —CO—CH$_2$—CO—;
x is 0 or 1;
$R_2$ is chosen from a saturated or unsaturated, optionally aromatic, linear, branched, or cyclic carbon-based divalent radicals of 1 to 30 carbon atoms, optionally comprising 1 to 18 heteroatoms chosen from O, N, S, F, Si, and P;
m is 0 or 1;
n ranges from 3 to 300;
$R_3$ is chosen from hydrogen and saturated or unsaturated, optionally aromatic, linear, branched, or cyclic carbon-based radicals of 1 to 30 carbon atoms, optionally comprising 1 to 20 heteroatoms chosen from O, N, S, F, Si, and P;
the at least one monomer of formula (I) has a molecular weight ranging from 500 to 13,000 g/mol; and
b) an amount ranging from 40% to 90% by weight of at least one essentially cationic monomer chosen from:
(i) cationic monomers of formula (IIa) and salts thereof,
(ii) amphoteric monomers of formula (IIc), salts thereof, amphoteric monomers of formula (IId), and salts thereof, and
(iii) a mixture of (1) at least one cationic monomer chosen from cationic monomers of formula (IIa) and salts thereof and (2) at least one at least one monomer chosen from (a) anionic monomers chosen from maleic anhydride, monomers of formula (IIb), and salts thereof, and
(b) amphoteric monomers chosen from monomers of formulae (IIc) and salts thereof, amphoteric monomers chosen from monomers of formulae (IId), and salts thereof;

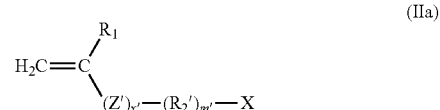

(IIa)

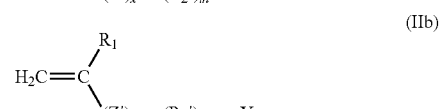

(IIb)

-continued

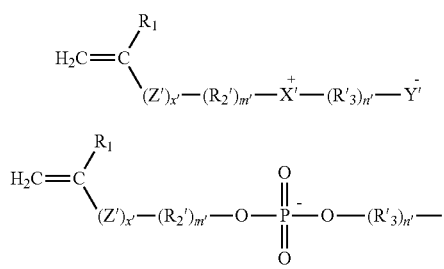

wherein:
R₁ is chosen from hydrogen; linear hydrocarbon-based radicals of the type $C_pH_{2p+1}$, wherein p ranges from 1 to 12; and branched hydrocarbon-based radicals of the type $C_pH_{2p+1}$, wherein p ranges from 1 to 12;
Z' is a divalent group chosen from —COO—, —CONH—, —CONCH₃—, —OCO—, —O—, —SO₂—, —CO—O—CO—, and —CO—CH₂—CO—;
x' is 0 or 1;
R₂' is chosen from a saturated or unsaturated, optionally aromatic, linear, branched, or cyclic divalent carbon-based radical of 1 to 30 carbon atoms, optionally comprising 1 to 18 heteroatoms chosen from O, N, S, F, Si, and P;
m' is 0 or 1;
X, in formula (IIa), is chosen from:
 (a) guanidino groups and amidino groups;
 (b) groups of formula —N(R₆)(R₇), groups of formula —P(R₆)(R₇), and groups of formula —P⁺R₆R₇R₈, wherein
  R₆, R₇, and R₈, which may be identical or different, are chosen from
   (i) hydrogen,
   (ii) linear, branched, or cyclic, saturated or unsaturated, optionally aromatic alkyl groups comprising from 1 to 18 carbon atoms, and optionally comprising 1 to 10 heteroatoms chosen from O, N, S, F, Si, and P; and
   (iii) R₆ and R₇ form together with the nitrogen or phosphorus atom to which they are attached a saturated or unsaturated, optionally aromatic ring comprising 5 to 8 atoms, wherein said ring may optionally be fused with at least one other saturated or unsaturated, optionally aromatic ring comprising 5 to 7 atoms; and
 (c) —R'₆—N—R'₇— groups, wherein R'₆ and R'₇ form together with the nitrogen atom a saturated or unsaturated, optionally aromatic ring comprising 5 to 8 atoms; said ring may optionally be fused with at least one other saturated or unsaturated, optionally aromatic ring comprising 5 to 7 atoms;
Y is chosen from —COOH, —SO₃H, —OSO₃H, —PO₃H₂, and —OPO₃H₂;
X'⁺ is a divalent group of formula —N⁺(R₆)(R₇)—, wherein R₆ and R₇, which may be identical or different, are chosen from (i) hydrogen, (ii) linear, branched, or cyclic, optionally aromatic alkyl groups comprising from 1 to 25 carbon atoms, optionally comprising 1 to 20 heteroatoms chosen from O, N, S, and P; and (iii) R₆ and R₇ form together with the nitrogen atom a saturated or unsaturated, optionally aromatic ring comprising 5 to 8 atoms, said ring optionally fused with at least one other saturated or unsaturated, optionally aromatic ring comprising 5 to 8 atoms;
Y" is chosen from —COO⁻, —SO₃⁻, —OSO₃⁻, —PO₃²⁻, and —OPO₃²⁻;
R'₃ is chosen from saturated or unsaturated, optionally aromatic, linear, branched, or cyclic divalent carbon-based radicals of 1 to 30 carbon atoms, optionally comprising 1 to 18 heteroatoms chosen from O, N, S, F, Si, and P;
n' ranges from 1 to 100;
X"⁺ is chosen from groups of formula —N⁺R₆R₇R₈, wherein R₆, R₇, and R₈, which may be identical or different, are chosen from (i) hydrogen, (ii) linear, branched, or cyclic, optionally aromatic alkyl groups comprising 1 to 18 carbon atoms, optionally comprising 1 to 5 heteroatoms chosen from O, N, S, and P; and (iii) R₆ and R₇ form together with the nitrogen atom a first saturated or unsaturated, optionally aromatic ring comprising 5 to 7 atoms, said ring optionally fused with at least one other saturated or unsaturated, optionally aromatic ring comprising 5 to 7 atoms;
and salts of said at least one copolymer.

32. The composition according to claim 31, wherein the copolymer is present in an amount ranging from 0.01% to 50% by weight of solids relative to the total weight of the composition.

33. The composition according to claim 31, wherein the physiologically acceptable medium comprises at least one constituent chosen from water; hydrophilic organic solvents; waxes, pasty fatty substances, gums of animal, plant, mineral, and synthetic origin; lipophilic organic solvents; oils of animal, plant, mineral, and synthetic origin; synthetic esters, ethers; pentaerythritol esters; fatty alcohols containing from 12 to 26 carbon atoms; partially hydrocarbon-based fluoro oils, silicone-based fluoro oils; volatile and nonvolatile, linear and cyclic silicone oils, which are liquid or pasty at room temperature; pigments, nacres, fillers, water-soluble dyes, and liposoluble dyes; polymers; auxiliary film-forming agents; surfactants; vitamins, fragrances, nacreous agents, thickeners, gelling agents, trace elements, softeners, sequestrants, fragrances, acidifying agents, basifying agents, preserving agents, sunscreens, antioxidants, hair-loss counteractants, antidandruff agents, propellants, and ceramides.

34. The composition according to claim 31, wherein said composition is in the form of a suspension; an optionally thickened oily solution; an optionally gelled oily solution; an oil-in-water emulsion, a water-in-oil emulsion, a multiple emulsion; a gel; a mousse; an oily gel; an emulsified gel; a dispersion of vesicles; a two-phase lotion; a multiphase lotion; a spray; a lotion, a cream, a pomade, a soft paste, an ointment, a cast solid, or a molded solid.

35. The composition according to claim 31, wherein said composition is in the form of a care product for facial skin, a care product for the body, a care product for lips, a care product for the hair, a makeup product for body facial skin, a makeup product for the body, a makeup product for lips, a makeup product for the hair, an antisun product, a self-tanning product, or a haircare product.

36. The composition according to claim 31, wherein said composition is in the form of a hair composition for at least one of holding the hairstyle and shaping the hair.

37. The composition according to claim 36, wherein the hair composition is in the form of a shampoo, a hairsetting gel, a hairsetting lotion, a blow-drying lotion, fixing composition, a styling compositions, a lacquer, a spray; a rinse-out hair conditioner, a leave-in hair conditioner, a composition for permanent-waving hair, a composition for relaxing hair, a composition for dyeing hair, a composition for bleaching hair, a rinse-out composition to be applied before dyeing hair, a rinse-out composition to be applied after dyeing hair, a rinse-out composition to be applied before bleaching hair, a rinse-out composition to be applied after bleaching hair, a rinse-out composition to be applied before permanent-waving hair, a rinse-out composition to be applied after permanent-waving hair, a rinse-out composition to be applied before relaxing hair, a rinse-out composition to be applied after relaxing hair, a rinse-out composition to be applied between two steps of a permanent-waving operation, or a rinse-out composition to be applied between two steps of a hair-relaxing operation.

38. The composition according to claim 31, comprising (weight %):
7.5% lauryl ether sulfate
2.5% cocobetaine amphoteric surfactant
5% cocopolyglucoside surfactant
1.5% polymer according to claim 1, and
qs 100% water;
said polymer comprising 50% by weight of poly(ethylene glycol) methacrylate with a molecular weight of 550 g/mol, and 50% by weight of dimethylaminopropyl-methacrylamide, and said polymer have been neutralized with betaine hydrochloride.

39. The composition according to claim 31, wherein said composition is in the form of a shampoo.

40. A cosmetic process for treating keratin materials, comprising: applying to the keratin materials a cosmetic composition,
wherein the cosmetic composition comprises in a physiologically acceptable medium, at least one copolymer, which is not cross-linked, consisting essentially of, as a weight percentage relative to the total weight of the polymer:
a) an amount ranging from 10% to 60% by weight of at least one monomer chosen from monomers of formula (I) and salts thereof:

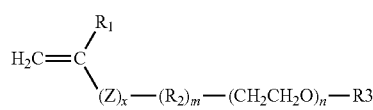

wherein:
R$_1$ is chosen from hydrogen, linear hydrocarbon-based radicals of the type C$_p$H$_{2p+1}$, wherein p ranges from 1 to 12, and branched hydrocarbon-based radicals of the type C$_p$H$_{2p+1}$, wherein p ranges from 1 to 12;
Z is a divalent group chosen from —COO—, —CONH—, —CONCH$_3$—, —OCO—, —O—, —SO$_2$—, —CO—O—CO—, and —CO—CH$_2$—CO—;
x is 0 or 1;
R$_2$ is chosen from a saturated or unsaturated, optionally aromatic, linear, branched, or cyclic carbon-based divalent radicals of 1 to 30 carbon atoms, optionally comprising 1 to 18 heteroatoms chosen from O, N, S, F, Si, and P;
m is 0 or 1;
n ranges from 3 to 300;
R$_3$ is chosen from hydrogen and saturated or unsaturated, optionally aromatic, linear, branched, or cyclic carbon-based radicals of 1 to 30 carbon atoms, optionally comprising 1 to 20 heteroatoms chosen from O, N, S, F, Si, and P;
the at least one monomer of formula (I) has a molecular weight ranging from 500 to 13,000 g/mol; and b) an amount ranging from 40% to 90% by weight of at least one essentially cationic monomer chosen from:
(i) cationic monomers of formula (IIa) and salts thereof,
(ii) amphoteric monomers of formula (IIc), salts thereof, amphoteric monomers of formula (IId), and salts thereof, and
(iii) a mixture of (1) at least one cationic monomer chosen from cationic monomers of formula (IIa) and salts thereof and (2) at least one at least one monomer chosen from (a) anionic monomers chosen from maleic anhydride, monomers of formula (IIb), and salts thereof, and
(b) amphoteric monomers chosen from monomers of formulae (IIc) and salts thereof, amphoteric monomers chosen from monomers of formulae (IId), and salts thereof;

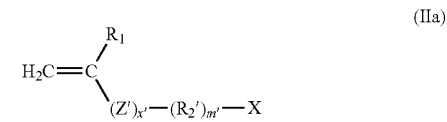

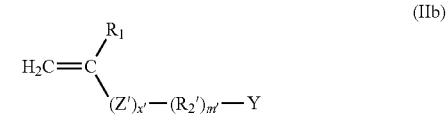

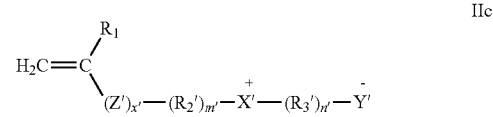

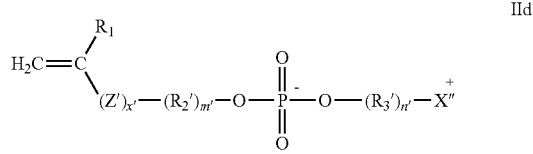

wherein:
R$_1$ is chosen from hydrogen; linear hydrocarbon-based radicals of the type C$_p$H$_{2p+1}$, wherein p ranges from 1 to 12; and branched hydrocarbon-based radicals of the type C$_p$H$_{2p+1}$, wherein p ranges from 1 to 12;
Z' is a divalent group chosen from —COO—, —CONH—, —CONCH$_3$—, —OCO—, —O—, —SO$_2$—, —CO—O—CO—, and —CO—CH$_2$—CO—;
x' is 0 or 1;
R$_2$' is chosen from a saturated or unsaturated, optionally aromatic, linear, branched, or cyclic divalent carbon-based radical of 1 to 30 carbon atoms, optionally comprising 1 to 18 heteroatoms chosen from O, N, S, F, Si, and P;
m' is 0 or 1;
X, in formula (IIa), is chosen from:
(a) guanidino groups and amidino groups;
(b) groups of formula —N(R$_6$)(R$_7$), groups of formula —P(R$_6$)(R$_7$), and groups of formula —P$^+$R$_6$R$_7$R$_8$,
wherein
R$_6$, R$_7$, and R$_8$, which may be identical or different, are chosen from
(i) hydrogen,
(ii) linear, branched, or cyclic, saturated or unsaturated, optionally aromatic alkyl groups comprising from 1 to 18 carbon atoms, and optionally comprising 1 to 10 heteroatoms chosen from O, N, S, F, Si, and P; and (iii) $R_6$ and $R_7$ form together with the nitrogen or phosphorus atom to which they are attached a saturated or unsaturated, optionally aromatic ring comprising 5 to 8 atoms, wherein said ring may optionally be fused with at least one other saturated or unsaturated, optionally aromatic ring comprising 5 to 7 atoms; and (c) —$R'_6$—N—$R'_7$— groups, wherein $R'_6$ and $R'_7$ form together with the nitrogen atom a saturated or unsaturated, optionally aromatic ring comprising 5 to 8 atoms; said ring may optionally be fused with at least one other saturated or unsaturated, optionally aromatic ring comprising 5 to 7 atoms;

Y is chosen from —COOH, —$SO_3H$, —$OSO_3H$, —$PO_3H_2$, and —$OPO_3H_2$;

$X'^+$ is a divalent group of formula —$N^+(R_6)(R_7)$—, wherein $R_6$ and $R_7$, which may be identical or different, are chosen from (i) hydrogen, (ii) linear, branched, or cyclic, optionally aromatic alkyl groups comprising from 1 to 25 carbon atoms, optionally comprising 1 to 20 heteroatoms chosen from O, N, S, and P; and (iii) $R_6$ and $R_7$ form together with the nitrogen atom a saturated or unsaturated, optionally aromatic ring comprising 5 to 8 atoms, said ring optionally fused with at least one other saturated or unsaturated, optionally aromatic ring comprising 5 to 8 atoms;

Y" is chosen from —$COO^-$, —$SO_3^-$, —$OSO_3^-$, —$PO_3^{2-}$, and —$OPO_3^{2-}$;

$R'_3$ is chosen from saturated or unsaturated, optionally aromatic, linear, branched, or cyclic divalent carbon-based radicals of 1 to 30 carbon atoms, optionally comprising 1 to 18 heteroatoms chosen from O, N, S, F, Si, and P;

n' ranges from 1 to 100;

$X''^+$ is chosen from groups of formula —$N^+R_6R_7R_8$, wherein $R_6$, $R_7$, and $R_8$, which may be identical or different, are chosen from (i) hydrogen, (ii) linear, branched, or cyclic, optionally aromatic alkyl groups comprising 1 to 18 carbon atoms, optionally comprising 1 to 5 heteroatoms chosen from O, N, S, and P; and (iii) $R_6$ and $R_7$ form together with the nitrogen atom a first saturated or unsaturated, optionally aromatic ring comprising 5 to 7 atoms, said ring optionally fused with at least one other saturated or unsaturated, optionally aromatic ring comprising 5 to 7 atoms;

and salts of said at least one copolymer.

* * * * *

UNITED STATES PATENT AND TRADEMARK OFFICE
CERTIFICATE OF CORRECTION

| | | |
|---|---|---|
| PATENT NO. | : 8,178,079 B2 | Page 1 of 1 |
| APPLICATION NO. | : 11/631119 | |
| DATED | : May 15, 2012 | |
| INVENTOR(S) | : Nathalie Mougin et al. | |

It is certified that error appears in the above-identified patent and that said Letters Patent is hereby corrected as shown below:

Claim 28, col. 37, line 52, "1 mP·s" should read -- 1 mPa·s --.

Claim 31, col. 40, line 1, "Y" is chosen from" should read -- $Y^{1-}$ is chosen from --.

Claim 40, col. 42, line 28, "IIc" should read -- (IIc) --.

Claim 40, col. 42, line 32, "IId" should read -- (IId) --.

Claim 40, col. 44, line 4, "Y" is chosen from" should read -- $Y^{1-}$ is chosen from --.

Signed and Sealed this

Fourteenth Day of August, 2012

David J. Kappos
*Director of the United States Patent and Trademark Office*